(12) United States Patent
Heikenfeld et al.

(10) Patent No.: US 10,506,968 B2
(45) Date of Patent: Dec. 17, 2019

(54) DEVICES CAPABLE OF FLUID SAMPLE CONCENTRATION FOR EXTENDED SENSING OF ANALYTES

(71) Applicants: Eccrine Systems, Inc., Cincinnati, OH (US); University of Cincinnati, Cincinnati, OH (US)

(72) Inventors: Jason Heikenfeld, Cincinnati, OH (US); Jacob A. Bertrand, Norwood, OH (US); Michael Brothers, Lebanon, OH (US); Andrew Jajack, Cincinnati, OH (US)

(73) Assignees: Eccrine Systems, Inc., Cincinnati, OH (US); University of Cincinnati, Cincinnati, OH (US)

( * ) Notice: Subject to any disclaimer, the term of this patent is extended or adjusted under 35 U.S.C. 154(b) by 0 days.

(21) Appl. No.: 15/966,476

(22) Filed: Apr. 30, 2018

(65) Prior Publication Data

US 2018/0289296 A1 Oct. 11, 2018

Related U.S. Application Data

(63) Continuation of application No. 15/770,262, filed as application No. PCT/US2016/058356 on Oct. 23, 2016.
(Continued)

(51) Int. Cl.
*A61B 5/145* (2006.01)
*A61B 5/00* (2006.01)
(Continued)

(52) U.S. Cl.
CPC .......... *A61B 5/4266* (2013.01); *A61B 5/0004* (2013.01); *A61B 5/1468* (2013.01);
(Continued)

(58) Field of Classification Search
None
See application file for complete search history.

(56) References Cited

U.S. PATENT DOCUMENTS 4,190,060 A 2/1980 Greenleaf et al.
4,542,751 A 9/1985 Webster et al.
(Continued)

FOREIGN PATENT DOCUMENTS

EP 0282349 A2 9/1988
EP 0453283 A1 10/1991
(Continued)

OTHER PUBLICATIONS

International Searching Authority, Search Report issued in corresponding International Application No. PCT/US2016/43771 dated Dec. 8, 2016, 4 pages.
(Continued)

*Primary Examiner* — Eric F Winakur
*Assistant Examiner* — Marjan Fardanesh

(57) ABSTRACT

The disclosed invention provides a fluid sensing device and method capable of collecting a fluid sample, concentrating the sample with respect to one or more target analytes, and measuring the target analyte(s) in the concentrated sample. The invention is also capable of determining the change in molarity of the fluid sample with respect to the target analyte(s), as the sample is concentrated by the device. The invention further includes a method for using a fluid sensing device to concentrate a fluid sample with respect to one or more target analytes. The disclosed method further includes the ability to correlate the measured target analyte concentration to a physiological condition of a device wearer, or of a fluid source.

10 Claims, 13 Drawing Sheets

Related U.S. Application Data

(60) Provisional application No. 62/269,447, filed on Dec. 18, 2015, provisional application No. 62/269,244, filed on Dec. 18, 2015, provisional application No. 62/245,638, filed on Oct. 23, 2015.

(51) Int. Cl.
    *G01N 33/50*     (2006.01)
    *A61B 10/00*     (2006.01)
    *A61B 5/1468*     (2006.01)
    *A61F 13/02*     (2006.01)
    *G01N 33/66*     (2006.01)
    *G01N 33/53*     (2006.01)
    *G01N 33/543*     (2006.01)

(52) U.S. Cl.
    CPC ...... *A61B 5/14517* (2013.01); *A61B 5/14521* (2013.01); *A61B 5/14532* (2013.01); *A61B 5/14546* (2013.01); *A61B 5/6833* (2013.01); *A61B 10/0012* (2013.01); *A61B 10/0064* (2013.01); *A61F 13/0246* (2013.01); *G01N 33/50* (2013.01); *G01N 33/5308* (2013.01); *G01N 33/5438* (2013.01); *G01N 33/66* (2013.01); *A61B 5/0002* (2013.01); *A61B 2010/0016* (2013.01)

(56) References Cited

U.S. PATENT DOCUMENTS

| | | |
|---|---|---|
| 4,756,314 A | 7/1988 | Eckenhoff et al. |
| 4,820,263 A | 4/1989 | Spevak et al. |
| 5,036,861 A | 8/1991 | Sembrowich et al. |
| 5,050,604 A | 9/1991 | Reshef et al. |
| 5,140,985 A | 8/1992 | Schroeder et al. |
| 5,246,003 A | 9/1993 | Delonzor |
| 5,437,999 A | 8/1995 | Diebold et al. |
| 5,438,984 A | 8/1995 | Schoendorfer |
| 5,556,789 A | 9/1996 | Goerlach-Graw et al. |
| 5,690,893 A | 11/1997 | Ozawa et al. |
| 5,814,599 A | 9/1998 | Mitragotri et al. |
| 5,817,012 A * | 10/1998 | Schoendorfer .... A61B 10/0035 600/362 |
| 5,944,662 A | 8/1999 | Schoendorfer |
| 6,175,752 B1 | 1/2001 | Say et al. |
| 6,198,953 B1 | 3/2001 | Webster et al. |
| 6,256,533 B1 | 7/2001 | Yuzhakov et al. |
| 6,269,265 B1 | 7/2001 | Anderson |
| 6,299,578 B1 | 10/2001 | Kumik et al. |
| 6,592,529 B2 | 7/2003 | Marett |
| 6,666,821 B2 | 12/2003 | Keimel |
| 7,044,911 B2 | 5/2006 | Drinan et al. |
| 7,190,986 B1 | 3/2007 | Hannula et al. |
| 7,219,534 B2 | 5/2007 | Campbell |
| 7,378,054 B2 | 5/2008 | Karmali |
| 7,383,072 B2 | 6/2008 | Edmonson et al. |
| 7,384,396 B2 | 6/2008 | Samuels et al. |
| 7,749,445 B2 | 7/2010 | Masters |
| 7,800,494 B2 | 9/2010 | Kim |
| 7,813,780 B2 | 10/2010 | Shah et al. |
| 7,842,234 B2 | 11/2010 | Lauks et al. |
| 7,959,791 B2 | 6/2011 | Kjaer et al. |
| 8,125,539 B2 | 2/2012 | Takashima |
| 8,128,889 B2 | 3/2012 | Fujimoto et al. |
| 8,252,248 B2 | 8/2012 | Kramer |
| 8,391,946 B2 | 3/2013 | Sugenoya et al. |
| 8,565,850 B2 | 10/2013 | Martinsen et al. |
| 8,593,287 B2 | 11/2013 | Hayter et al. |
| 8,617,067 B2 | 12/2013 | Jain et al. |
| 9,133,024 B2 | 9/2015 | Phan et al. |
| 9,867,539 B2 | 1/2018 | Heikenfeld et al. |
| 2002/0091312 A1 | 7/2002 | Bemer et al. |
| 2003/0135100 A1 | 7/2003 | Kim et al. |
| 2003/0201194 A1 | 10/2003 | Heller et al. |
| 2004/0215098 A1 | 10/2004 | Barton |
| 2004/0249310 A1 | 12/2004 | Shartle et al. |
| 2004/0260154 A1 | 12/2004 | Sidelnik et al. |
| 2004/0267189 A1 | 12/2004 | Mavor et al. |
| 2005/0069925 A1 | 3/2005 | Ford et al. |
| 2005/0106713 A1 | 5/2005 | Phan et al. |
| 2005/0177035 A1 | 8/2005 | Botvinick et al. |
| 2005/0192528 A1 | 9/2005 | Tapper |
| 2005/0197554 A1 | 9/2005 | Polcha |
| 2005/0228297 A1 | 10/2005 | Banet et al. |
| 2005/0280531 A1 | 12/2005 | Fadem et al. |
| 2006/0009697 A1 | 1/2006 | Banet et al. |
| 2006/0062852 A1 | 3/2006 | Holmes |
| 2006/0127964 A1 | 6/2006 | Ford et al. |
| 2006/0253011 A1 | 11/2006 | Edmonson et al. |
| 2006/0254341 A1 | 11/2006 | Campbell |
| 2007/0027383 A1 | 2/2007 | Peyser et al. |
| 2007/0032731 A1 | 2/2007 | Lovejoy et al. |
| 2007/0179371 A1 | 8/2007 | Peyser et al. |
| 2008/0015494 A1 | 1/2008 | Santini, Jr. et al. |
| 2008/0045816 A1 | 2/2008 | Jang et al. |
| 2008/0154179 A1 | 6/2008 | Cantor et al. |
| 2008/0286349 A1 | 11/2008 | Nomoto et al. |
| 2008/0306362 A1 | 12/2008 | Davis |
| 2009/0076345 A1 | 3/2009 | Manicka et al. |
| 2009/0159442 A1 | 6/2009 | Collier et al. |
| 2009/0204008 A1 | 8/2009 | Beilin |
| 2009/0270704 A1 | 10/2009 | Peyser et al. |
| 2009/0308136 A1 * | 12/2009 | Wang ............... A61B 5/082 73/23.4 |
| 2010/0044224 A1 | 2/2010 | Kataky |
| 2010/0063372 A1 | 3/2010 | Potts et al. |
| 2010/0130843 A1 | 5/2010 | Caceres Galvez et al. |
| 2010/0132485 A1 | 6/2010 | Erez et al. |
| 2010/0198521 A1 | 8/2010 | Haick |
| 2011/0004072 A1 | 1/2011 | Fletcher et al. |
| 2011/0054273 A1 | 3/2011 | Omoda |
| 2011/0079521 A1 | 4/2011 | Revol-Cavalier |
| 2011/0118656 A1 | 5/2011 | Eckhoff et al. |
| 2011/0178380 A1 | 7/2011 | Chowdhury |
| 2011/0196283 A1 | 8/2011 | Imran et al. |
| 2011/0208458 A1 | 8/2011 | Pinter et al. |
| 2011/0275918 A1 | 11/2011 | Yamashita et al. |
| 2012/0004570 A1 | 1/2012 | Shimizu et al. |
| 2012/0028283 A1 | 2/2012 | Hoss et al. |
| 2012/0119906 A1 | 5/2012 | Kountotsis |
| 2012/0123220 A1 | 5/2012 | Iyer et al. |
| 2012/0165626 A1 | 6/2012 | Irina et al. |
| 2012/0191147 A1 | 7/2012 | Rao et al. |
| 2012/0209226 A1 | 8/2012 | Simmons et al. |
| 2012/0229661 A1 | 9/2012 | Sekiguchi et al. |
| 2012/0277697 A1 | 11/2012 | Haghgooie et al. |
| 2012/0285829 A1 | 11/2012 | Mount et al. |
| 2012/0317430 A1 | 12/2012 | Rahman et al. |
| 2013/0006079 A1 | 1/2013 | Feldman et al. |
| 2013/0010108 A1 | 1/2013 | Hashizume et al. |
| 2013/0013028 A1 | 1/2013 | Kriksunov et al. |
| 2013/0053668 A1 | 2/2013 | Lin |
| 2013/0079605 A1 | 3/2013 | Bandaru et al. |
| 2013/0099937 A1 | 4/2013 | Azimi |
| 2013/0108667 A1 | 5/2013 | Soikum et al. |
| 2013/0123595 A1 | 5/2013 | Currie et al. |
| 2013/0183399 A1 | 7/2013 | Blow et al. |
| 2013/0245388 A1 | 9/2013 | Rafferty et al. |
| 2013/0306491 A1 | 11/2013 | Briman et al. |
| 2013/0317318 A1 | 11/2013 | Tartz et al. |
| 2013/0317333 A1 | 11/2013 | Yang et al. |
| 2014/0012114 A1 | 1/2014 | Zevenbergen et al. |
| 2014/0025000 A1 | 1/2014 | Currie et al. |
| 2014/0038306 A1 * | 1/2014 | Berthier ............. B01L 3/50273 436/172 |
| 2014/0046149 A1 * | 2/2014 | Simpson ........... A61B 5/14532 600/316 |
| 2014/0206977 A1 | 7/2014 | Bahney et al. |
| 2014/0221792 A1 | 8/2014 | Miller et al. |
| 2014/0275862 A1 | 9/2014 | Kennedy |
| 2014/0276220 A1 | 9/2014 | Briscoe et al. |
| 2014/0343371 A1 | 11/2014 | Sowers, II et al. |
| 2015/0057515 A1 | 2/2015 | Hagen et al. |

(56) References Cited

U.S. PATENT DOCUMENTS

| | | |
|---|---|---|
| 2015/0112164 A1 | 4/2015 | Heikenfeld et al. |
| 2015/0112165 A1 | 4/2015 | Heikenfeld |
| 2015/0289820 A1 | 4/2015 | Miller et al. |
| 2016/0058354 A1 | 3/2016 | Phan et al. |
| 2016/0066828 A1 | 3/2016 | Phan et al. |
| 2016/0157768 A1 | 6/2016 | Braig et al. |
| 2017/0100035 A1 | 4/2017 | Heikenfeld |
| 2017/0100071 A1 | 4/2017 | Heikenfeld |
| 2017/0215773 A1 | 8/2017 | Heikenfeld et al. |

FOREIGN PATENT DOCUMENTS

| | | | |
|---|---|---|---|
| EP | 1575010 A1 | 9/2005 | |
| EP | 1637889 A1 | 3/2006 | |
| EP | 2551784 A1 | 1/2013 | |
| EP | 2783725 A1 | 10/2014 | |
| WO | 1990011519 A1 | 10/1990 | |
| WO | 1994014062 A1 | 6/1994 | |
| WO | 2000014535 A1 | 3/2000 | |
| WO | 2001088525 A1 | 11/2001 | |
| WO | WO-03052865 A2 * | 6/2003 | ............ G01N 13/04 |
| WO | 2006133101 A2 | 12/2006 | |
| WO | 2007097754 A1 | 8/2007 | |
| WO | 2007146047 A1 | 12/2007 | |
| WO | 2008058014 A2 | 5/2008 | |
| WO | 2008083687 A1 | 7/2008 | |
| WO | 2008095940 A1 | 8/2008 | |
| WO | 2009004001 A1 | 1/2009 | |
| WO | 2009052321 A2 | 4/2009 | |
| WO | 2010017578 A1 | 2/2010 | |
| WO | 2011008581 A2 | 1/2011 | |
| WO | 2011117952 A1 | 9/2011 | |
| WO | 2013111409 A1 | 8/2013 | |
| WO | 2013181436 A1 | 12/2013 | |
| WO | 2014001577 A1 | 1/2014 | |
| WO | 2014025430 A3 | 5/2014 | |
| WO | 2015058065 A1 | 4/2015 | |
| WO | 2016007944 A2 | 1/2016 | |
| WO | 2016049019 A1 | 3/2016 | |
| WO | 2016090189 A1 | 6/2016 | |
| WO | 2016130905 A1 | 8/2016 | |
| WO | 2016138087 A1 | 9/2016 | |
| WO | 2017019602 A1 | 2/2017 | |
| WO | 2017070640 A1 | 4/2017 | |

OTHER PUBLICATIONS

International Searching Authority, Written Opinion issued in corresponding International Application No. PCT/US2016/43771 dated Dec. 8, 2016, 9 pages.

International Searching Authority, Search Report and Written Opinion issued in corresponding International Application No. PCT/US2016/58356 dated Jan. 6, 2017, 15 pages.

International Searching Authority, Search Report and Written Opinion issued in corresponding International Application No. PCT/US2016/58357 dated Jan. 19, 2017, 9 pages.

International Searching Authority, Search Report and Written Opinion issued in corresponding International Application No. PCT/US2017/047808 dated Nov. 6, 2017, 10 pages.

* cited by examiner

DEVICES CAPABLE OF FLUID SAMPLE CONCENTRATION FOR EXTENDED SENSING OF ANALYTES

CROSS-REFERENCE TO RELATED APPLICATIONS

This application is a continuation of U.S. application Ser. No. 15/770,262, filed Apr. 23, 2018; and claims priority to PCT/US16/58356, filed Oct. 23, 2016; U.S. Provisional No. 62/245,638, filed Oct. 23, 2015; U.S. Provisional No. 62/269,244, filed Dec. 18, 2015, and U.S. Provisional No. 62/269,447, filed Dec. 18, 2015, the disclosures of which are hereby incorporated by reference herein in their entirety.

BACKGROUND OF THE INVENTION

Non-invasive biosensing technologies have enormous potential for several medical, fitness, and personal well-being applications. The sweat ducts can provide a route of access to many of the same biomarkers, chemicals, or solutes that are carried in blood and can provide significant information enabling one to diagnose ailments, health status, toxins, performance, and other physiological attributes even in advance of any physical sign. Sweat has many of the same analytes and analyte concentrations found in blood and interstitial fluid. Interstitial fluid has even more analytes nearer to blood concentrations than sweat does, especially for larger sized and more hydrophilic analytes (such as proteins).

While bio-monitoring fluids offer their greatest potential when used a source of continuous information about the body, the technological challenges of accomplishing such continuous monitoring are considerable. For example, many techniques that work well in a laboratory are difficult to implement in a wearable device. This is especially true for laboratory techniques used to measure analytes that typically emerge in sweat, interstitial fluid, or other fluid below the detection limit for available sensors. To overcome this challenge, devices and methods for concentrating fluid samples inside a wearable device are needed, and disclosed herein.

Many of the drawbacks and limitations stated above can be resolved by creating novel and advanced interplays of chemicals, materials, sensors, electronics, microfluidics, algorithms, computing, software, systems, and other features or designs, in a manner that affordably, effectively, conveniently, intelligently, or reliably brings biofluid sensing technology into proximity with a fluid as it is generated.

SUMMARY OF THE INVENTION

The disclosed invention provides a fluid sensing device capable of collecting a fluid sample, concentrating the sample with respect to a target analyte, and measuring the target analyte in the concentrated sample. The invention is also capable of determining the change in molarity of the fluid sample with respect to the target analyte, as the sample is concentrated by the device.

BRIEF DESCRIPTION OF THE DRAWINGS

The objects and advantages of the present disclosure will be further appreciated in light of the following detailed descriptions and drawings in which.

DEFINITIONS

Figure 1:
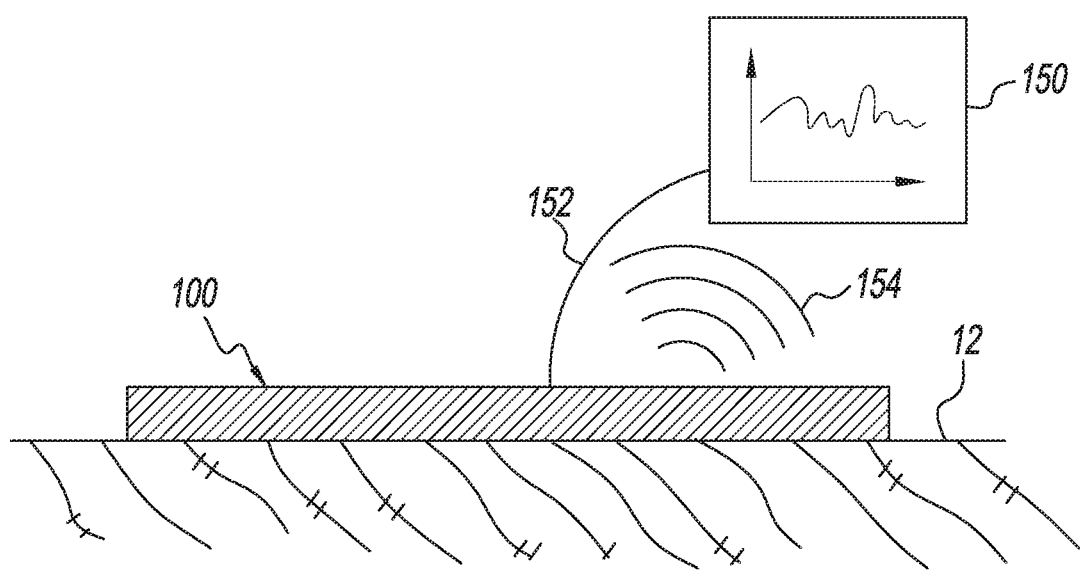
FIG. 1 is a depiction of at least a portion of a wearable device for sweat biosensing.

As used herein, "sweat" or "sweat biofluid" means a biofluid that is primarily sweat, such as eccrine or apocrine sweat, and may also include mixtures of biofluids such as sweat and blood, or sweat and interstitial fluid, so long as advective transport of the biofluid mixtures (e.g., flow) is primarily driven by sweat.

As used herein, "biofluid" may mean any human biofluid, including, without limitation, sweat, interstitial fluid, blood, plasma, serum, tears, and saliva. A biofluid may be diluted with water or other solvents inside a device because the term biofluid refers to the state of the fluid as it emerges from the body.

As used herein, "fluid" may mean any human biofluid, or other fluid, such as water, including without limitation, groundwater, sea water, freshwater, etc., or other fluids.

As used herein, "continuous monitoring" means the capability of a device to provide at least one sensing and measurement of fluid collected continuously or on multiple occasions, or to provide a plurality of fluid measurements over time.

As used herein, "chronological assurance" is an assurance of the sampling rate for measurement(s) of sweat (or other biofluid or fluid), or solutes in sweat, being the rate at which measurements can be made of new sweat or its new solutes as they originate from the body. Chronological assurance may also include a determination of the effect of sensor function, or potential contamination with previously generated sweat, previously generated solutes, other fluid, or other measurement contamination sources for the measurement(s).

As used herein, "determined" may encompass more specific meanings including but not limited to: something that is predetermined before use of a device; something that is determined during use of a device; something that could be a combination of determinations made before and during use of a device.

As used herein, "sweat sampling rate" is the effective rate at which new sweat, or sweat solutes, originating from the sweat gland or from skin or tissue, reaches a sensor that measures a property of sweat or its solutes. Sweat sampling rate, in some cases, can be far more complex than just sweat generation rate. Sweat sampling rate directly determines, or is a contributing factor in determining, the chronological assurance. Times and rates are inversely proportional (rates having at least partial units of 1/seconds), therefore a short or small time required to refill a sweat volume can also be said to have a fast or high sweat sampling rate. The inverse of sweat sampling rate (1/s) could also be interpreted as a "sweat sampling interval(s)". Sweat sampling rates or intervals are not necessarily regular, discrete, periodic, discontinuous, or subject to other limitations. Like chronological assurance, sweat sampling rate may also include a determination of the effect of potential contamination with previously generated sweat, previously generated solutes, other fluid, or other measurement contamination sources for the measurement(s). Sweat sampling rate can also be in whole or in part determined from solute generation, transport, advective transport of fluid, diffusion transport of solutes, or other factors that will impact the rate at which new sweat or sweat solutes reach a sensor and/or are altered by older sweat or solutes or other contamination sources. Sensor response times may also affect sampling rate.

As used herein, "sweat stimulation" is the direct or indirect causing of sweat generation by any external stimulus, the external stimulus being applied for the purpose of stimulating sweat. Sweat stimulation, or sweat activation, can be achieved by known methods. For example, sweat stimulation can be achieved by simple thermal stimulation, chemical heating pad, infrared light, by orally administering a drug, by intradermal injection of drugs such as carbachol, methylcholine or pilocarpine, and by dermal introduction of such drugs using iontophoresis. A device for iontophoresis may, for example, provide direct current and use large lead electrodes lined with porous material, where the positive pole is dampened with 2% pilocarpine hydrochloride and the negative one with 0.9% NaCl solution. Sweat can also be controlled or created by asking the device wearer to enact or increase activities or conditions that cause them to sweat. These techniques may be referred to as active control of sweat generation rate.

As used herein, "sweat generation rate" is the rate at which sweat is generated by eccrine sweat glands. Sweat generation rate is typically measured by the flow rate from each gland in nL/min/gland. In some cases, the measurement is then multiplied by the number of sweat glands from which sweat is being sampled to calculate the sweat volume sampled per unit time.

As used herein, "fluid sampling rate" is the effective rate at which new fluid, or fluid solutes, originating from the fluid source, reaches a sensor that measures a property of the fluid or its solutes. Fluid sampling rate directly determines, or is a contributing factor in determining, the chronological assurance. Times and rates are inversely proportional (rates having at least partial units of 1/seconds), therefore a short or small time required to refill a fluidic volume can also be said to have a fast or high fluid sampling rate. The inverse of fluid sampling rate (1/s) could also be interpreted as a "fluid sampling interval(s)". Fluid sampling rates or intervals are not necessarily regular, discrete, periodic, discontinuous, or subject to other limitations. Like chronological assurance, fluid sampling rate may also include a determination of the effect of potential contamination with previously generated fluid, previously generated solutes, other fluid, or other measurement contamination sources for the measurement(s). Fluid sampling rate can also be in whole or in part determined from solute generation, transport, advective transport of fluid, diffusion transport of solutes, or other factors that will impact the rate at which new fluid or fluid solutes reach a sensor and/or are altered by older fluid or solutes or other contamination sources. Sensor response times may also affect sampling rate.

As used herein, "measured" can imply an exact or precise quantitative measurement and can include broader meanings such as, for example, measuring a relative amount of change of something. Measured can also imply a binary measurement, such as 'yes' or 'no', present/not present type measurements.

As used herein, "fluidic volume" is the fluidic volume in a space that can be defined multiple ways. Fluidic volume may be the volume that exists between a sensor and the point of generation of a fluid or a solute moving into or out of the fluid from the body or from other sources. Fluidic volume can include the volume that can be occupied by fluid between: the sampling site on the skin and a sensor on the skin, where the sensor has no intervening layers, materials, or components between it and the skin; or the sampling site on the skin and a sensor on the skin where there are one or more layers, materials, or components between the sensor and the sampling site on the skin.

As used herein, "solute generation rate" is simply the rate at which solutes move from the body or other sources into a fluid. "Solute sampling rate" includes the rate at which these solutes reach one or more sensors.

As used herein, "microfluidic components" are channels in polymer, textiles, paper, or other components known in the art of microfluidics for guiding movement of a fluid or at least partial containment of a fluid.

As used herein, "state void of fluid" means a fluid sensing device component, such as a space, material or surface, that can be wetted, filled, or partially filled by fluid, when the component is entirely or substantially (e.g., >50%) dry or void of fluid.

As used herein, "advective transport" is a transport mechanism of a substance, or conserved property by a fluid, that is due to the fluid's bulk motion.

As used herein, "diffusion" is the net movement of a substance from a region of high concentration to a region of low concentration. This is also referred to as the movement of a substance down a concentration gradient.

As used herein, a "sample concentrator" is any portion of a device, material, subsystem, or other component that can be utilized to increase the molarity of at least one fluid analyte, at least in part by removing a portion of the water that was originally with the at least one analyte when it exited the body.

"EAB sensor" means an electrochemical aptamer-based biosensor that is configured with multiple aptamer sensing elements that, in the presence of a target analyte in a fluid sample, produce a signal indicating analyte capture, and which signal can be added to the signals of other such sensing elements, so that a signal threshold may be reached that indicates the presence or concentration of the target analyte. Such sensors can be in the forms disclosed in U.S. Pat. Nos. 7,803,542 and 8,003,374 (the "Multi-capture Aptamer Sensor" (MCAS)), or in U.S. Provisional Application No. 62/523,835 (the "Docked Aptamer Sensor" (DAS)).

As used herein, the term "analyte-specific sensor" is a sensor specific to an analyte and performs specific chemical recognition of the analyte's presence or concentration (e.g., ion-selective electrodes, enzymatic sensors, electrochemical aptamer-based sensors, etc.). For example, sensors that sense impedance or conductance of a fluid, such as sweat, are excluded from the definition of analyte-specific sensor because sensing impedance or conductance merges measurements of all ions in sweat (i.e., the sensor is not chemically selective; it provides an indirect measurement). Sensors could also be optical, mechanical, or use other physical/chemical methods which are specific to a single analyte. Further, multiple sensors can each be specific to one of multiple analytes.

DETAILED DESCRIPTION OF THE INVENTION

The disclosed invention applies at least to any type of fluid sensor device that measures fluid, fluid generation rate, fluid chronological assurance, its solutes, solutes that transfer into fluid from skin, tissue, or other source, a property of or things on the surface of skin, or properties or things beneath the skin. The invention applies to fluid sensing devices which can take on forms including patches, bands, straps, portions of clothing, wearables, or any suitable mechanism that reliably brings sweat stimulating, fluid collecting, and/or fluid sensing technology into intimate proximity with fluid as it is generated. Some embodiments of the invention utilize adhesives to hold the device near the skin, but devices could also be held by other mechanisms that hold the device secure against the skin, such as a strap or embedding in a helmet.

Certain embodiments of the invention show sensors as simple individual components. It is understood that many sensors require two or more electrodes, reference electrodes, or additional supporting technology or features that are not captured in the description herein. Sensors are preferably electrical in nature, but may also include optical, chemical, mechanical, or other known biosensing mechanisms. Sensors can be in duplicate, triplicate, or more, to provide improved data and readings. Sensors may be referred to by what the sensor is sensing, for example: a sweat sensor; an impedance sensor; a fluid volume sensor; a sweat generation rate sensor; and a solute generation rate sensor. Certain embodiments of the disclosed invention show sub-components of what would be fluid sensing devices with more sub-components needed for use of the device in various applications, which are obvious (such as a battery), and for purpose of brevity and focus on inventive aspects are not explicitly shown in the diagrams or described in the embodiments of the invention. As a further example, many embodiments of the invention could benefit from mechanical or other means known to those skilled in wearable devices, patches, bandages, and other technologies or materials affixed to skin, to keep the devices or sub-components of the skin firmly affixed to skin or with pressure favoring constant contact with skin or conformal contact with even ridges or grooves in skin, and are included within the spirit of the disclosed invention. The present application has specification that builds upon PCT/US13/35092, the disclosure of which is hereby incorporated herein by reference in its entirety.

With reference to FIG. 1, a sweat sensing device 100 is placed on or near skin 12. In an alternate embodiment, the sweat sensing device may be fluidically connected to skin or regions near skin through microfluidics or other suitable techniques. Device 100 is in wired communication 152 or wireless communication 154 with a reader device 150. In one embodiment of the invention, the reader device 150 would be a smart phone or portable electronic device. In alternate embodiments, device 100 and reader device 150 can be combined. In further alternate embodiments, communication 152 or 154 is not constant and could be a simple one-time data download from device 100 once it has completed its measurements of sweat.

Figure 2:
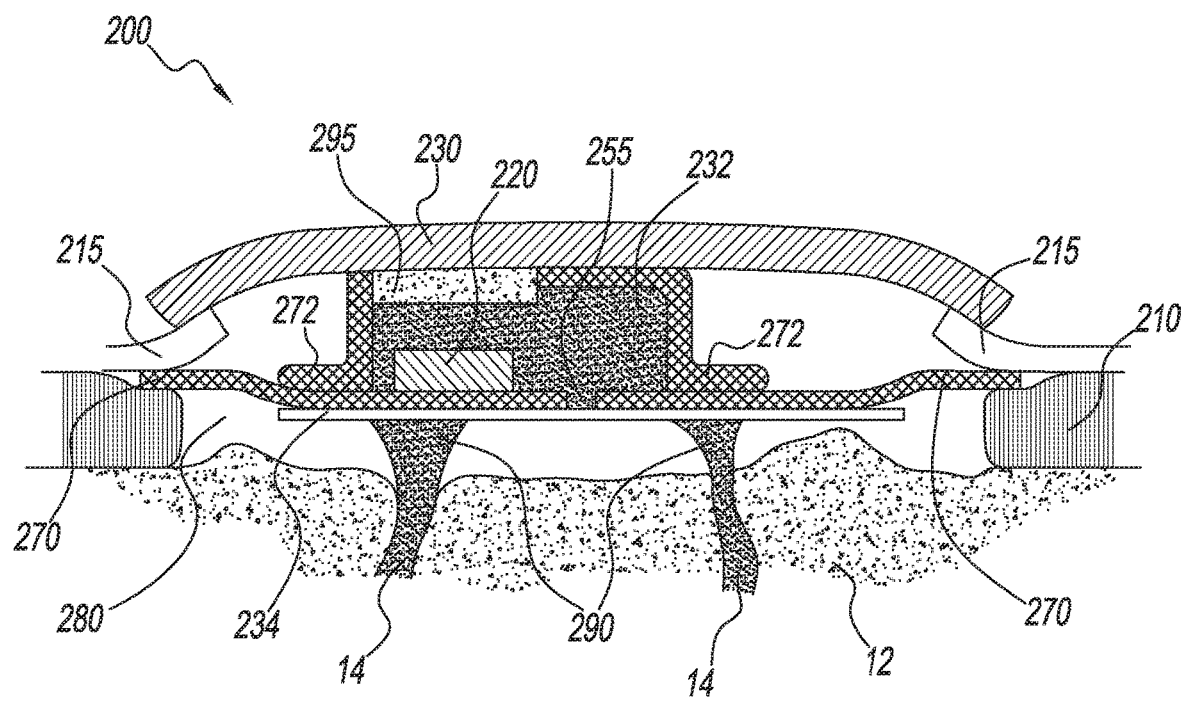
FIG. 2 is an example embodiment of at least a portion of a device capable of fluid sample concentration.

With reference to FIG. 2, a device 200 provides a reduced fluidic volume 280 between a wearer's skin 12 and at least one analyte-specific sensor 220, as disclosed in PCT/US2015/032893. The fluidic volume 280 is bounded by a fluid impermeable substrate 270 such as PET, and an adhesive layer 210, which also functions to secure the device to the skin. Material 270 has an opening in the center 255, to allow fluid to access the sensor 220. Adhesives can be pressure sensitive, liquid, tacky hydrogels, which promote robust electrical, fluidic, and iontophoretic contact with skin. The device 200 further includes fluid impermeable materials 215 and 272, where 215 may also serve as a substrate for fabrication (e.g., one or more layers shown in FIG. 2 could be fabricated on the substrate, for example a Kapton substrate for flexible electronics). The locations of sweat ducts 14 are also noted.

The device 200 is also configured to provide a reduced wicking volume, as disclosed in PCT US2016/43771. Accordingly, the device includes a sweat collector 234, which draws sweat through opening 255, and creates volume reduced pathway(s) 290 between the ducts and the opening 255. The sweat collector 234 is in fluidic communication with a fluid sample coupler 232, which carries sweat past the sensor 220. Sensor 220 could be any sensor specific to an analyte in sweat, such as an ion-selective electrode, enzymatic sensor, electrochemical aptamer sensor, etc. The fluid sample coupler 232 is in fluid communication with a fluid sample pump 230, which is comprised of a textile, paper, or hydrogel, and that serves to maintain fluid flow through the device. The sweat collector 234 must be adequately thin so that its fluidic volume is less than the fluidic volume of the wicking space 280. As an example of a proper implementation of the sweat collector 234, the wicking space 280 could have an average height of 50 μm due to skin roughness, or more if hair or debris is present. The wicking material could be a 5 μm thick layer of screen-printed nanocellulose with a weak binder and or a thin hydrogel material to hold the cellulose together. Importantly, in terms of strength of capillary force, material 232 should have greater capillary force than material 230, which in turn should have greater capillary force than wicking space 280. In a preferred embodiment, fluid sample coupler 232 would have the greatest wicking force relative to the other wicking materials, such as 234 and 230, so that sensor 220 remains wetted with sweat.

With further reference to FIG. 2, the device 200 also includes a sample concentrator 295. In one embodiment of the invention, the sample concentrator 295 is a dialysis membrane that is permeable to inorganic ions but impermeable to small molecules and proteins. In other embodiments, the sample concentrator may be any membrane or material that is at least porous to water, but that is not substantially porous to the analyte that is to be concentrated. As sweat flows onto fluid sample pump 230 by wicking through the concentrator membrane 295, solutes are concentrated in fluid sample coupler 232. The device may be configured to concentrate a target analyte in the fluid sample by at least 2× higher than the unconcentrated molarity. Depending on the application, the target analyte may be concentrated at least 10×, 100×, or 1000× higher than the unconcentrated molarity. The fluid sample coupler 232 could be hydrogel, textile, or other suitable wicking material. Analyte-specific sensor 220 may be, for example, two or more electrochemical sensors for cortisol and didehydroepiandrosterone (DHEA) to measure the ratio of these two biomarkers in sweat. This ratio is a well-known marker of many conditions, see, e.g., http://metabolichealing.com/cortisol-dhea-the-major-hormone-balance/, and furthermore allows meaningful sensing without having to determine the molarity of the fluid sample concentrated by the sample concentrator 295.

In an alternate embodiment, an osmosis membrane can be used as the sample concentrator 295, where the membrane is water-permeable, but is impermeable to electrolytes, such as $K^+$. Because sweat $K^+$ concentration does not vary significantly with sweat rate, the sensor 220 could measure $K^+$ and another analyte, such as cortisol, to determine the molarity of the fluid sample, and therefore allow accurate back-calculation of the original cortisol concentration. Embodiments of the disclosed invention may accordingly be configured with a first sensor specific to a first fluid analyte and a second sensor specific to a second fluid analyte, wherein both the first and second analytes are concentrated. Similarly, additional sensors may be added to measure additional concentrated analytes. In other embodiments, sweat conductivity could be measured and used to determine the molarity, although this method would be less reliable, since sweat conductivity is more variable with sweat generation rate.

Figure 3A:
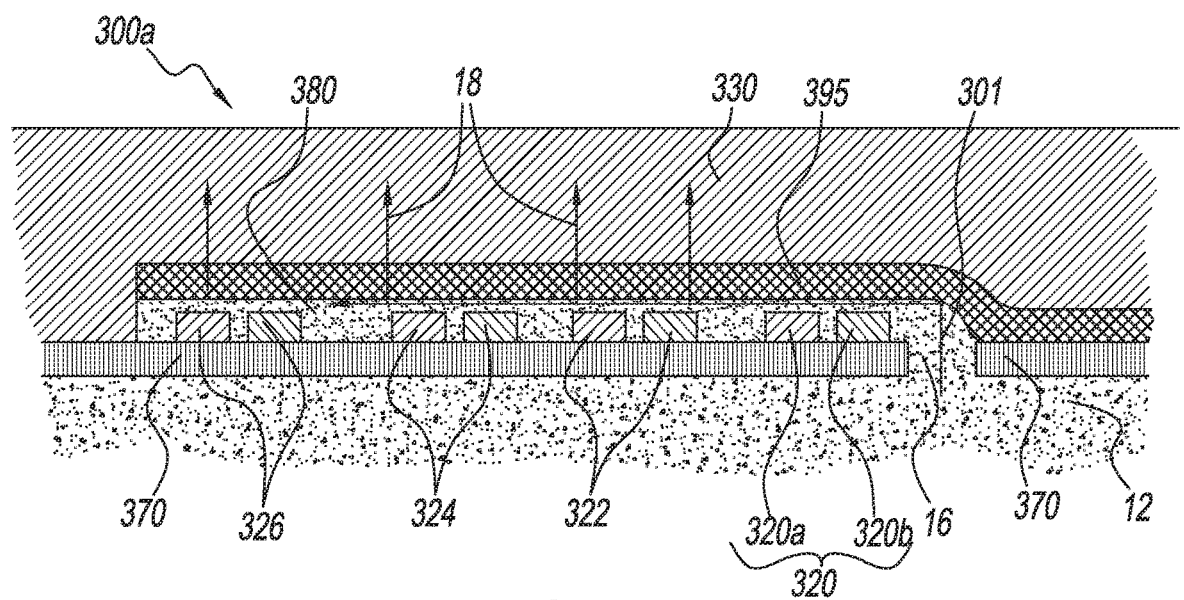
FIGS. 3A and 3B is an example embodiment of at least a portion of a device capable of fluid sample concentration.

With reference to FIG. 3A, where like numerals refer to like features of previous figures, a microchannel 380 is created and filled with a fluid sample 16 between sample concentrator membrane 395 and fluid impermeable material or film 370. The microchannel 380 includes at least one pair of sensors 320a and 320b, that form a sensor pair 320. For example, a first sensor 320a may be for $K^+$, and a second sensor 320b may be for cortisol. Sensor pair 320 measures the unconcentrated sweat concentrations of $K^+$ and cortisol as they emerge from the skin 12. As fluid 16 flows leftward through the microchannel 380 in the direction of the arrow 301, water 18 from the fluid diffuses into the fluid sample pump 330, which may be a hydrogel, a desiccant, salt, or microfluidic wicking material, by osmosis or capillary wicking force. By this mechanism, the fluid sample 16 becomes more concentrated as it moves through the microchannel 380. Sensor pairs 322, 324, 326 likewise measure $K^+$ and cortisol, but at increasing concentrations as the fluid sample 16 becomes more concentrated (i.e., loses more water through sample concentrator 395). The $K^+$ sensor is used to predict the molarity of the sweat sample 16 and therefore correct the cortisol reading for the increasing molarity. One will recognize that the channel flow volume will decrease as the sample 16 moves through the microchannel 380 along the arrow 301, and in some cases the flow velocity or pressure will become too low to allow reliable measurement (e.g., diffusion or backflow will contaminate the sample). Therefore, in one example, the channel 380 may be tapered in at least one dimension along the channel length moving right to left. With such a configuration, as the fluid sample 16 flows from right to left, the sample's deceleration from fluid loss may be reduced, fluid velocity may remain steady, or fluid velocity may actually increase, as the volume of the microchannel decreases (as will be illustrated in a later figure). The sample concentrator membrane 395 could also have a surface charge in water, which would tend to reject permeation by ions such as $K^+$. The invention may include a plurality of analyte-specific sensors for detecting at least one target analyte, wherein at least two of said plurality of sensors comprise a first sensor group, and at least two of said plurality of sensors comprise a second sensor group, and wherein the first sensor group measures the target analyte in a less concentrated fluid sample, and the second sensor group measures the target analyte in a more concentrated fluid sample.

Figure 3B:
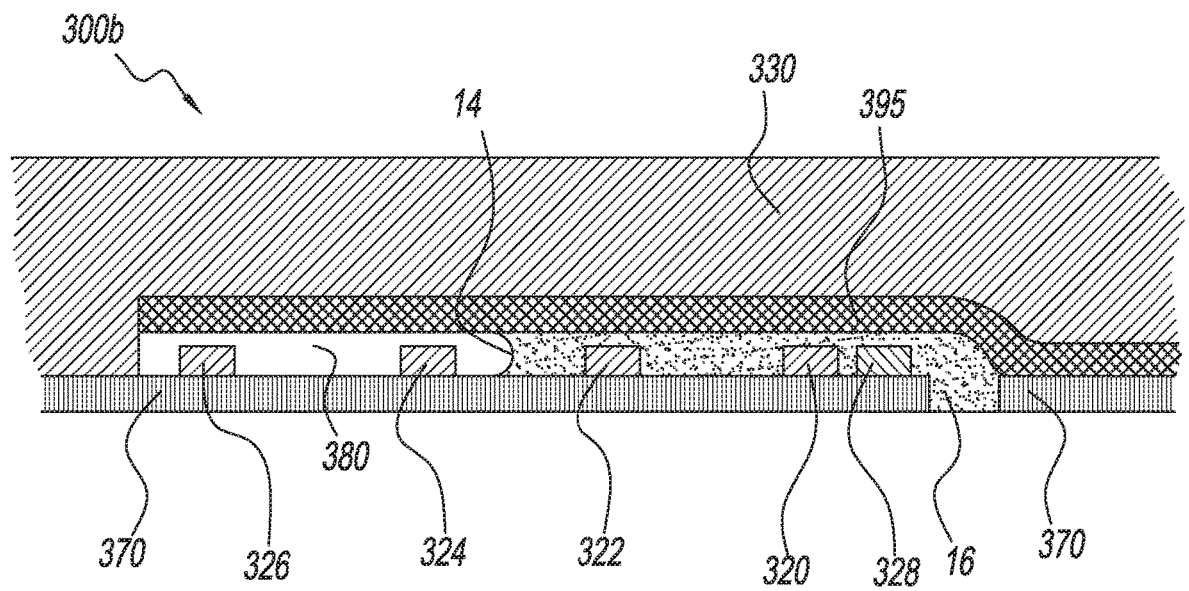

With reference to FIG. 3B, the device 300b is similar to device 300a of FIG. 3A with several exceptions. As an initial matter, the sensors 320, 322, 324, 326 could be similar to those described previously, or may detect the presence of a fluid sample 16 by potential or conductance, where the fluid 16 is in its original, unconcentrated form, or in a concentrated form. A channel, tube, or other capillary component 380 is created between concentrator membrane 395 and water-impermeable film 370. Alternately, the channel could be formed entirely out of a tube of membrane material, such as used for the membrane 395 (e.g., a small dialysis tube). Multiple arrangements are possible, so long as they satisfy the general inventive aspects described herein. As shown, the advancing edge 14 of fluid 16 is concave and moving toward fluid sample pump 330. The fluid sample pump 330 could be a gel, a desiccant, and the membrane 395 could be membranes like previously taught for FIG. 2 or porous Teflon membrane filled with air, or other material which provides at least one gas filled pathway. Membrane 395 could therefore allow water to pass into the air as water vapor (evaporation). If evaporation is relied upon, then concentrator 395 may not need to be permi-selective to solutes in fluid, but rather would help define the microfluidic channel 380. A fluid sample 16 could be collected, fill the channel, and water or solutes that are not of interest for sensing may be extracted through concentrator membrane 395. As water is lost, the fluid sample 16 reduces in volume, and the sensors 320, 322, 324, 326 can use a volume measurement to predict how much fluid sample 16 was collected initially and how much sample 16 has been concentrated. Therefore, the disclosed invention may include at least one sensor for volumetric measurement. Other sensor arrangements to determine the molarity of the sample 16 may also be possible, and the use of sensors 320, 322, 324, 326 are one non-limiting example.

In another example embodiment, sensor 328 may sense a target analyte, and the analyte's actual molarity can be calculated based on successive sensor 320, 322, 324, 326 measurements that estimate the volume of water extracted through the membrane 395 into the fluid sample pump 330. For the most reliable and repeatable results, at least one microfluidic gate (not shown) may be added to allow a fluid sample 16 to enter the device, then the gate could close to prevent, or adequately slow, introduction of new fluid into the microchannel 380. Integration of microfluidic gates will be further taught in later figures and embodiments. The aspect ratios of the microchannel 380 shown in FIG. 3 are for diagrammatic purposes only, and the channel 380 could be very long with a small cross section, e.g., a coiled tube.

Figure 4:
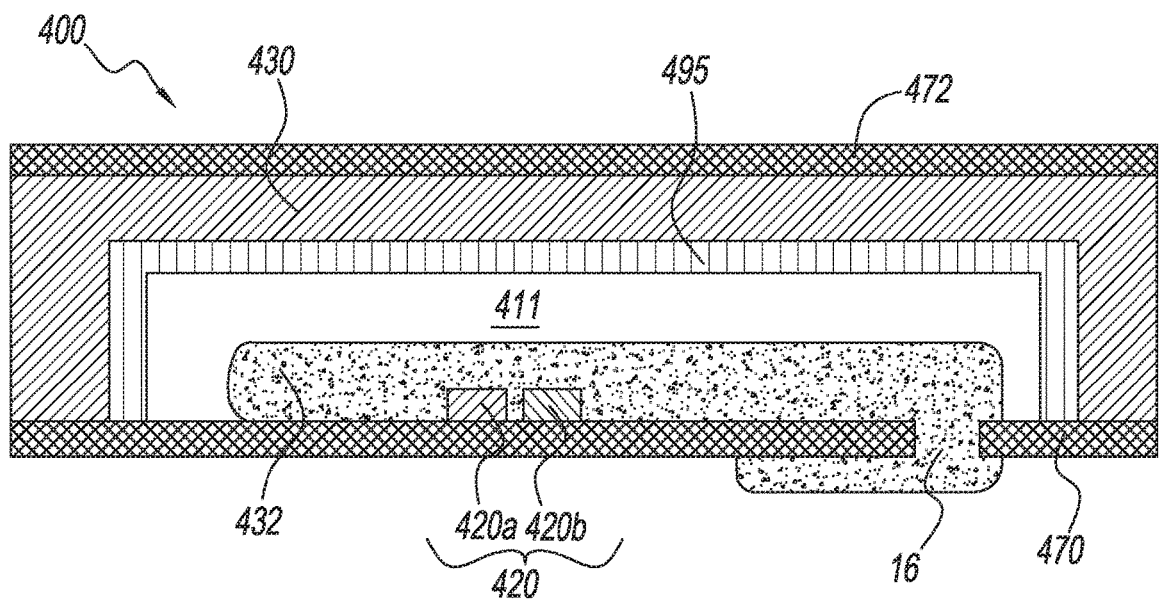
FIG. 4 is an example embodiment of at least a portion of a device capable of fluid sample concentration.

With reference to FIG. 4, where like numerals refer to like features of previous figures, a fluid sample coupler 432 wicks and holds a fluid sample 16. Alternately, fluid sample coupler 432 could be a channel, capillary, or wetted surface with fluid 16 at least partially exposed and unconfined (allowing evaporation). Outside the fluid sample coupler 432 is an air or gas gap 411, followed by a water vapor porous concentrator or membrane material 495, followed by a fluid sample pump 430 comprised of, e.g., a desiccant. The air gap 411 is used, because in some cases, small ions or other target analytes will penetrate through an osmosis membrane as described in previous embodiments. Therefore, the air gap 411 will only allow exit of volatile compounds such as water, and retain more solutes than a membrane could, in some cases. An external film 472 that is not water vapor permeable is also provided, to prevent desiccant from becoming saturated due to moisture or water vapor from outside the device 400. In an alternate embodiment, the device may omit the pump and film, and will therefore operate by evaporation of the fluid sample into ambient air (not shown). Other beneficial features may be included (not shown) such as a heater to promote evaporation, for example. The heater could be integrated onto substrate 470 between fluid sample coupler 432 and substrate 470, and could be, for example, a simple heater based on electrical resistance. To prevent the device wearer from feeling heat on their skin, low thermal conductivity or thermal isolation materials may also be added between the heater and skin (not shown). The disclosed invention may include at least one air gap as a pathway for evaporation concentration of fluid, and may include at least one desiccant that receives water evaporated from the fluid, and may include at least one heater that promotes evaporation of water from the fluid. Similarly, vacuum pressure could also be applied to promote evaporation.

Figure 5:
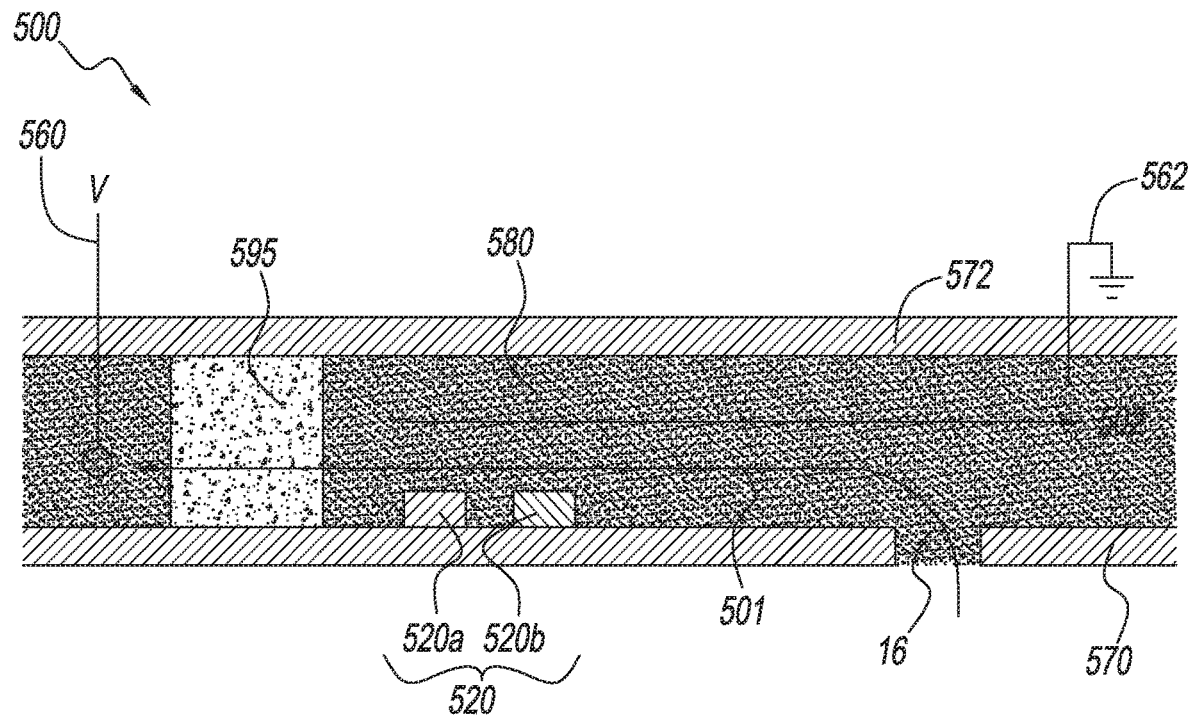
FIG. 5 is an example embodiment of at least a portion of a device capable of fluid sample concentration.

With reference to FIG. 5, where like numerals refer to like features of previous figures, a microfluidic channel 580 is formed between film or material 570 and film or material 572. Like previous embodiments, the concentrator membrane 595 is permi-selective in terms of which analytes may pass through it, or concentrator 595 could pass primarily only water. In such embodiments, sample concentration is achieved by one of several active microfluidic mechanisms, such as electrophoresis, iontophoresis, electro-osmosis, dielectrophoresis, electro-wetting, pressure-driven advective flow, etc. For example, as shown in FIG. 5, if the driving force were electrical, electrodes 560 and 562 could provide voltage or current, and therefore drive a flow of fluid sample 16 containing a target analyte leftward in the direction of arrow 501. Concentrator membrane 595 would block the target analyte, (e.g., glucose), causing an increased molar concentration of the target analyte. In some embodiments, the membrane may also be configured to block a second target analyte for calibration purposes, (e.g., testosterone). The molarities of the two target analytes would be measured through use of sensors 520a and 520b, respectively. Such a device 500 could be used to take multiple measurements of the target analytes, the performance improved by removing the fluid sample after sensing by reversing the voltage, or by using other flow driving means, so that the fluid sample 16 moves away in the direction of arrow 502. In some embodiments, the present disclosure may include at least one component capable of creating a reversible flow of fluid. In other embodiments, the invention may include at least one component for applying a non-equilibrium pressure (e.g., electrical, mechanical, etc.) to reverse the fluid sample 16 flow.

Figure 6:
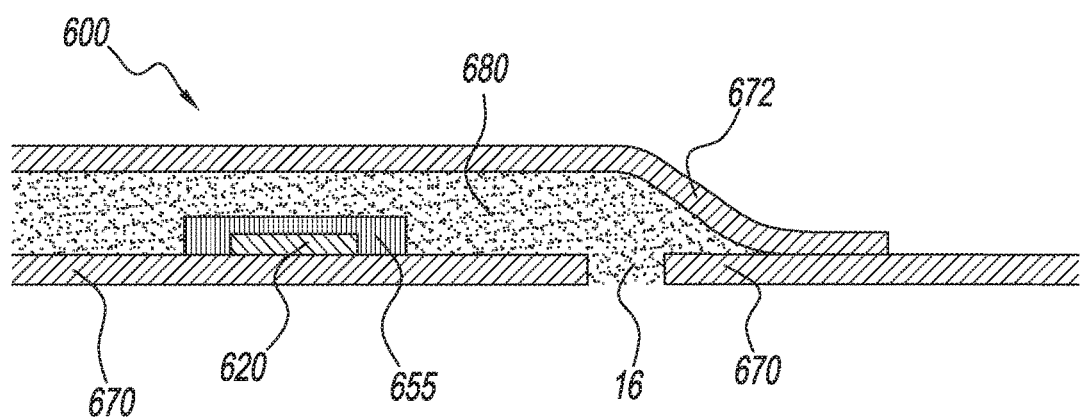
FIG. 6 is an example embodiment of at least a portion of a device capable of fluid sample concentration.

With reference to FIG. 6, where like numerals refer to like features of previous figures, a microfluidic channel 680 is formed between film or material 670 and film or material 672. A sensor 620 is coated or surrounded by an immiscible material 655. Immiscible material 655 is non-dissolvable in the fluid sample 16. The immiscible material could be an ionic liquid, a hydrocarbon, a liquid crystal, a porous polymer, or any material which has a distribution coefficient with respect to water or other fluid which is greater than 2. For example, if immiscible material 655 were a fluid or gel that is more hydrophobic than water, then hydrophobic solutes in sweat or interstitial fluid, such as cortisol, lipids, or other solutes, would passively concentrate into immiscible material 655. The distribution coefficient is k and can be predetermined or measured, and the target analyte molarity that occurs will equal k, and therefore the target analyte sweat concentration can be easily predicted. Distribution coefficients can be in the 1's to 10's even 100's or more. An example would be electrochemical sensing of hemoglobin using glassy carbon surrounded by an ionic liquid. The analytes which have the greatest distribution coefficients with respect to sweat generally make electrochemical sensing more challenging, and therefore other methods of sensing, such as optical techniques may be preferred.

Figure 7:
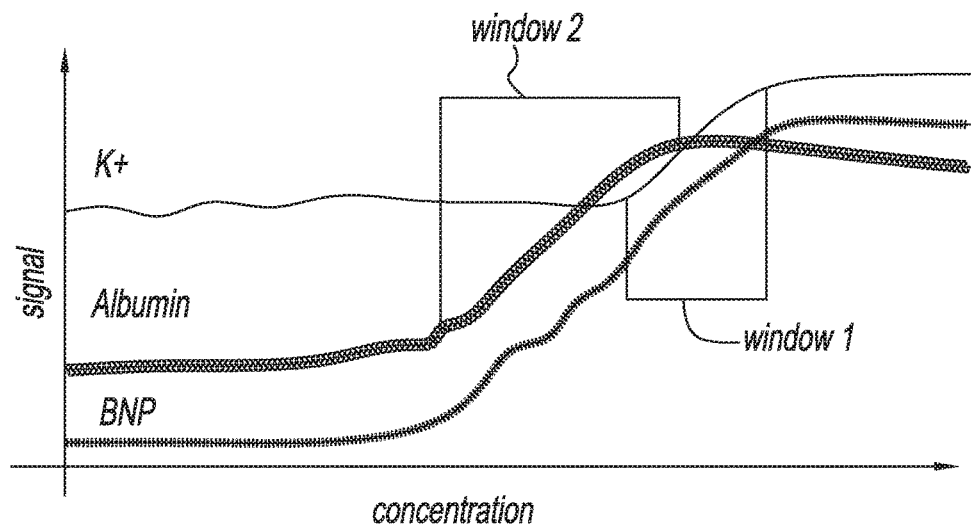
FIG. 7 is an illustrated data plot of how the disclosed invention could be utilized.

With reference to FIG. 7, a graph is provided to illustrate one example of how the invention could be utilized. At low concentrations of an analyte, there is no signal change (the concentration is below the limits of detection) and at high concentrations, sensor signals can become saturated. The fluid sensing device may measure continuously or repeatedly to determine whether a proper sensing window had been achieved. For example, because $K^+$ maintains a fairly consistent sweat concentration relative to changes in sweat rate, $K^+$ could be used to determine the molarity of a concentrated sweat sample. This molarity measurement would indicate when an adequate concentration of another analyte, for example the peptide BNP, had been reached to enable an accurate measurement of its concentration. The $K^+$ measurement could then be used to back-calculate the BNP molarity in unconcentrated sweat. This is represented by window 1 in FIG. 7. Similarly, window 2 represents the range for which sweat concentrations of albumin would be used to determine the molarity increase of the sweat sample (because albumin concentration is fairly constant in blood). In one embodiment, an analyte-specific sensor may be continually operating to measure $K^+$, albumin, or another marker with fairly consistent sweat concentration, and other analyte-specific sensors would be activated only when a target analyte reached an appropriate concentration window. As will be taught in later embodiments, devices can also adapt the amount of sample concentration to maintain the sweat sample in the sensing windows as exemplified in FIG. 7.

Figure 8:
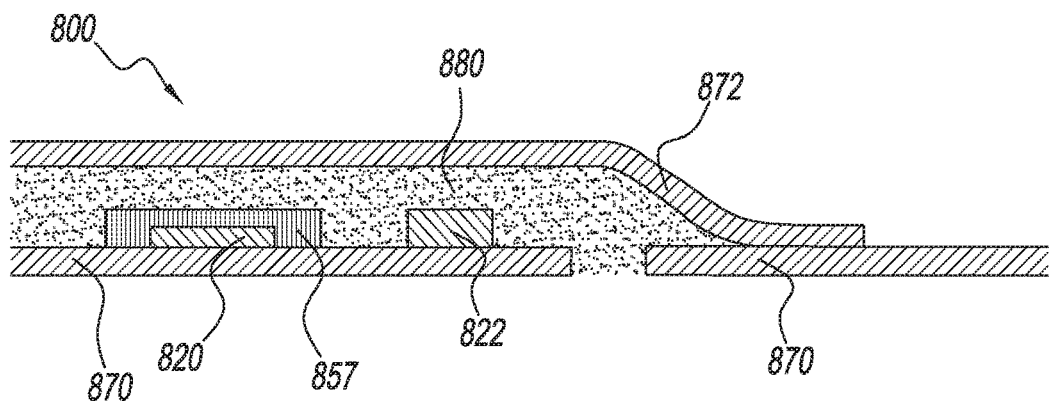
FIG. 8 depicts an example embodiment of at least a portion of a device capable of fluid sample concentration.

With reference to FIG. 8, where like numerals refer to like features of previous figures, an amperometric sensor 820 and enzymatic material 857 is provided, along with a secondary sensor 822 which can measure fluid collection rate or fluid generation rate. For example, sensor 822 could be a thermal flow sensor operable in the range of 0.1 to 100 nL/min. Amperometric sensors are a type of analyte-consuming sensor, which reduce the amount of target analyte present in the fluid sample by performing an enzymatic conversion of the analyte, allowing measurement to occur. Other sensor technologies that consume or irreversibly alter the target analyte may also be used, especially those where sample volume can limit proper sensor function. Such sensor modalities are useful for measuring analytes like ethanol, glucose, or lactate. Assume, for example, that sensor 820 and material 857 are configured to facilitate the amperometric sensing of ethanol. During the measurement process, the analyte undergoes a two or more step process of enzymatic conversion, followed by a charge transfer to or from sensor 820. Since analyte-consuming sensors deplete the available analyte, if they are continuously operated, the steady-state detection signal may remain below the sensor's lower limit of detection, or below the level of background electrical noise.

An embodiment of the disclosed invention allows continuous sensing with analyte-consuming sensors by periodically sampling only when a chronologically assured new (or unmeasured) fluid sample is introduced to the sensor 820, and after a sufficient amount of analyte is enzymatically converted. The flow sensor 822 measures the rate at which new fluid enters the device 800, which allows the device to determine when the fluid sample is fully refreshed. Once the chronologically assured new fluid sample is introduced to sensor 820, and after at least some of the target analyte is enzymatically converted, the device activates sensor 820 to sense amperometric charge. As a result, instead of continuous measurement, the sensor 820 only operates periodically, which allows the analyte concentration to build during intervals between measurements, which increases the signal relative to the lower limit of detection, or relative to the noise level. In another embodiment, flow sensor 822 is absent, and sensor 820 may be activated periodically, or according to a predetermined schedule. This example embodiment merely illustrates one device configuration that improves the function of enzymatic and other analyte-consuming sensors when used with sample concentration.

Figure 9:
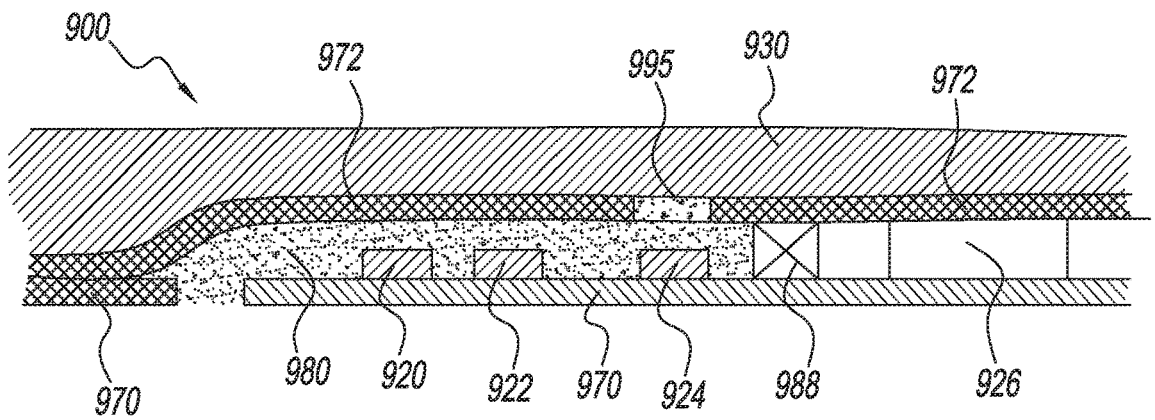
FIG. 9 depicts an example embodiment of at least a portion of a device capable of fluid sample concentration.

With reference to FIG. 9, where like numerals refer to like features of previous figures, a device 900 includes a plurality of different sensor types that may be used at different times. The device depicted in FIG. 9 is an illustrative example, but the invention is not so limited (multiple analytes may be sensed using various device, material, and sensor configurations). Sensor 920 is for estrogen, and sensor 922 is for progesterone, both of which have electrochemical aptamer-based sensors configured to operate at the analytes' natural concentration ranges found in sweat. In the appropriate concentrations, these analytes can indicate the likelihood of impending female ovulation. Concentrator membrane 995 is permeable to solutes with size<1000 Da, and relatively impermeable to solutes with size>1000 Da, such that estrogen or progesterone are able to pass through the membrane 995 (generally, size selective). Sensor 924 is any sensor type that measures one of an analyte, flow, or property of sweat, which can be used to indicate the fluid sample's increase in molarity for analytes>1000 Da. Note, the microchannel 980 near substrate or material 970 and membrane 995 could be larger than shown, and therefore, this, like other embodiments, should not be strictly interpreted by the apparent dimensions in the figures. The device 900 is applied, for example, at 8 PM, and the next day, the user has selected 8 PM as a moment to determine the likelihood of ovulation within the next several hours. During device operation, sensors 920 and 922 measure the likelihood of ovulation by measuring estrogen and progesterone concentrations. Sensors 920 and 922 are able to measure estrogen and progesterone molarities in an unconcentrated sweat sample, because these analytes are ~300 Da in size, and will pass through membrane 995 into fluid sample pump 930. As sweat continues to enter the channel 980, larger solutes unable to pass through the concentrator 995 will become concentrated in the sweat sample. At a size of ~30,000 Da luteinizing hormone will be unable to pass through the membrane 995, and with therefore be one of the solutes concentrated. At around 8 PM, a microfluidic gate 988, which could be any gate type known to those skilled in the art of microfluidics, allows the concentrated sweat sample to flow onto sensor 926, which could be any type of sensor for luteinizing hormone, for example a lateral flow assay such as are commonly used in commercial urinary test strips for ovulation. If sensor 926 is a lateral flow assay, larger sample volumes may be required. Luteinizing hormone, like other proteins, is likely dilute in sweat compared to blood, but a device that collected sweat for 24 hours could collect and concentrate a sweat sample with a sufficient number of luteinizing hormone molecules to be detected by sensor 926. Sensor 924 may be used to inform the amount of concentration that has occurred, but would not be necessary if a simple qualitative measurement of the analyte is required. After stabilization, sensor 926 would then inform the user of the likelihood of ovulation.

This is an example of a device of the present disclosure that may be configured a number of different ways, and may include at least one microfluidic gate between a first sensor and the fluid sample that is being concentrated, an electrochemical sensor or a non-electrochemical sensor, a sensor for concentrated samples or a sensor for non-concentrated samples, or a sensor that does not receive a sample of fluid until one of the following occurs: 1) another sensor provides an input; 2) a scheduled time; or 3) a user provides an input or request. For example, if concentration of estrogen or progesterone were to change significantly in sweat then signals from those sensors could go to electronics (not shown) which would then further trigger gate 988 to open or close as needed.

Figure 10:
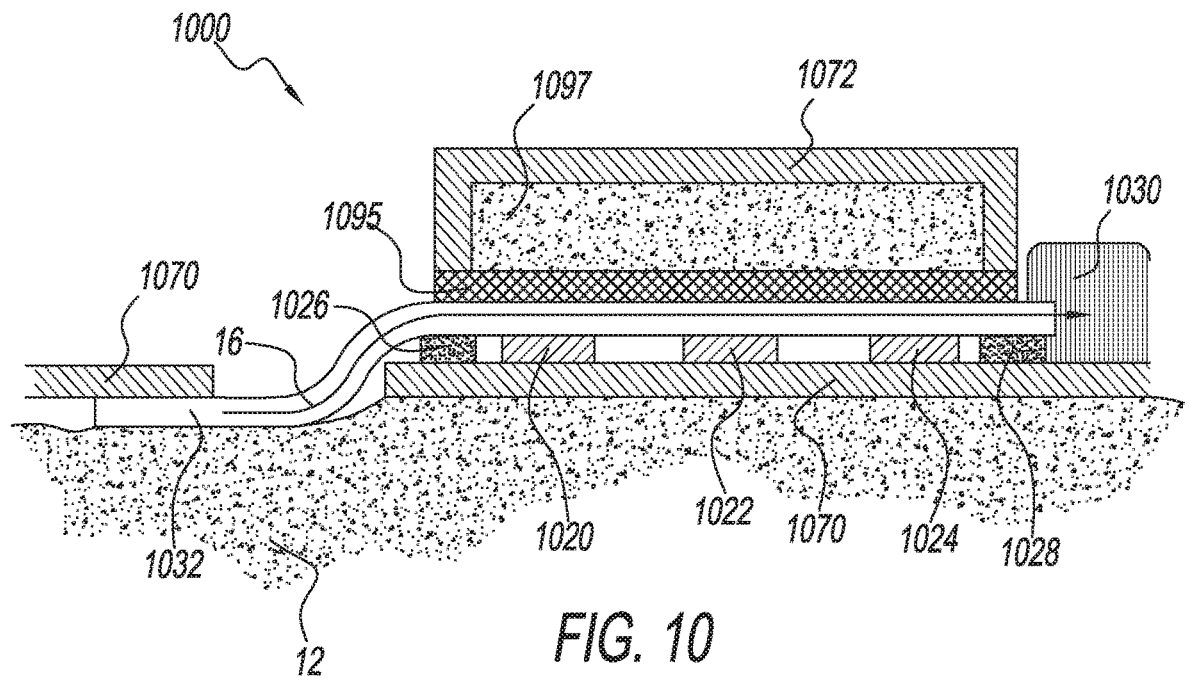
FIG. 10 depicts an example embodiment of at least a portion of a device capable of fluid sample concentration.

With reference to FIG. 10, where like numerals refer to like features of previous figures, a device 1000 includes a concentrator membrane 1095, such as a forward osmosis membrane, and a concentrator pump 1097. The concentrator pump 1097 could be comprised of a draw solution or material, like sucrose dissolved in water, or a dry draw material, e.g., a wicking material, hydrogel, dissolvable polymer, a large-molecule salt, dry sucrose, or other suitable materials capable of exerting a wicking or osmotic force or pressure. The device further includes a sweat collector 1032, which could be a cellulose film or a network of hydrophilic microchannels; fluid impermeable material or films 1070, 1072; a fluid sample pump 1030; fluid flow rate sensors 1026, 1028; and fluid analyte sensors 1020, 1022, 1024. As sweat is moved 16 along sweat collector 1032, water and certain sweat-abundant solutes will pass through the concentrator membrane 1095 and into the concentrator pump 1097, while the remaining sweat sample flows toward the fluid sample pump 1030. The sweat sample will accordingly become more concentrated with respect to the target analyte as it moves in the direction of the arrow 16 along the sweat collector toward the fluid sample pump 1030. The flow rate sensors 1026, 1028 could be mass thermal flow sensors, or other suitable sensor type. As the sweat sample is concentrated by the concentrator membrane 1095, the geometry of the sweat collector 1032 and the ratio of fluid flow at flow sensors 1026 and 1028 could be used to determine the total amount of fluid concentration achieved by the device. The disclosed invention may include at least one flow sensor or a plurality of flow sensors for determining the degree of concentration. The sensors 1020, 1022, and 1024 could be for the same analytes, or different analytes, or could be different sensor modalities, for example, they could all be configured to sense for cortisol. Sweat cortisol concentration would be sufficient to allow measurement as long as at least one of the sensors 1020, 1022, 1024 experienced the necessary concentration range for an accurate cortisol reading.

Therefore, the disclosed invention may include a plurality of sensors for the same analyte, wherein at least one of said sensors measures a fluid sample that is more concentrated with respect to a target analyte than the fluid sample measured by at least one other of said sensors.

With further reference to FIG. 10, in an alternate embodiment of the disclosed invention, each of sensors 1020, 1022, 1024 could further contain two subsensors, one subsensor may be an electrochemical aptamer-based sensor for albumin, and the other subsensor may be an electrochemical aptamer-based sensor for luteinizing hormone. Because an individual's blood albumin concentration is usually constant, albumin could serve as a reference analyte for a target analyte that does show significant blood concentration variation (e.g., luteinizing hormone). Such an arrangement and use of two sensors can help increase the analytical accuracy of the device, especially since albumin and luteinizing hormone are large, and most types of filtration membranes that can be used in the disclosed invention would be impervious to their passage. Therefore, the invention may include at least one sensor specific to a reference analyte, where said reference analyte is concentrated to a similar degree as a target analyte, at least one sensor specific to the target analyte, and where concentrations of the reference and target analytes can be compared.

In another alternate embodiment, a first sensor can measure the fluid concentration of a reference analyte (e.g., albumin) before sample concentration, and a second sensor can measure the reference analyte concentration after or during sample concentration. Sample concentration as disclosed complicates analyte sensing, because most sensing modalities have a limited dynamic range (e.g., EAB sensors typically have a dynamic range of between −40× to +40× the aptamer's linear range $K_D$), which means that sample concentration (e.g., 10× or more) and biological concentration variances (e.g., 10× or more) can put analyte concentrations outside the dynamic range of the sensors. Therefore, sensors may be arranged along the sweat collector 1032 so that their dynamic ranges increase as sweat moves in the direction of the arrow 16. For example, sensor 1020 and its subsensors for albumin and luteinizing hormone could have a dynamic range centered at lower concentrations than the dynamic range for sensor 1022 and its subsensors for albumin and luteinizing hormone, and 1024 could have dynamic ranges centered at the highest concentrations. Embodiments of the disclosed invention may, therefore, include a first sensor for measuring a fluid analyte concentration, and a second sensor for the fluid analyte concentration, where the second sensor has a dynamic range of detection that is centered on a higher concentration ($K_D$) than that of the first sensor.

With further reference to FIG. 10, some materials comprising the concentrator membrane 1095 need to be stored in a primarily wet condition, and some membrane materials need to be stored in a primarily dry condition. For dry storage materials, concentrator pump material 1097, such as a draw solution, can be introduced near or at the time of first use by numerous methods, including injection by a syringe, or use of foil burst valves, like those used in other types of point-of-care diagnostic cartridges.

With further reference to FIG. 10, in an alternate embodiment, the degree to which a target analyte will be concentrated by the device while in use is easily predictable. Generally, achieving analytical accuracy becomes more challenging as fluid generation rates or fluid sampling intervals change, because the amount of concentration produced by the concentrator pump disclosed herein varies with variations in fluid flow rates through the device. The flow rate of, e.g., sweat through the device depends on the inlet flow from skin, the outlet to the fluid sample pump 1030, and a flow of at least water into the concentrator pump 1097. To reduce this variability, in some embodiments, the device is configured so that the degree of sample concentration for a target analyte is predetermined or predictable based on the specific ion concentrations or the total ionic strength/osmolarity in the sample fluid or in the concentrator pump 1097. For example, the concentrator membrane 1095 could be a membrane that allows mainly water transport, but is impervious to the target analyte, lactate. Sensor 1026 could measure a fluid lactate concentration before the sample is concentrated. Next, assume that the incoming sweat flows into the device at a sweat generation rate that produces ~20 mM concentration of lactate in the concentrated sample. Concentrator pump 1097 would be configured with a draw solution containing 400 mM in lactate concentration and have other solutes that match natural sweat concentrations or that match the general (total equivalent) osmolality of sweat, except for the additional osmolality contribution of the 400 mM lactate concentration. The concentrator membrane would be long enough or large enough (e.g. mm's or cm's long) so that the fluid sample in sweat collector 1032 loses water until it also reaches 400 mM lactate concentration by water loss, resulting in ~20× concentration. Importantly, this degree of concentration could be accurately determined prior to device use because a sensor 1020 measures the unconcentrated fluid lactate concentration and the concentrator pump 1027 has a draw solution with a known lactate concentration (purposely configured). Alternately, the target analyte need not be measured in unconcentrated fluid if the analyte concentration varies little in the fluid, or if an application does not require a high degree of analytical accuracy.

In an alternate embodiment, a device's target analyte concentration can be predetermined or predicted where the device measures the ionic strength or conductivity in the sample fluid and uses a draw solution with a near constant osmotic pressure greater than that of the fluid (at least 2×). Maximum analytical accuracy will therefore be achieved if sensors 1022, 1024 for target analytes are near the end of the concentrator membrane 1095 (near the fluid sample pump 1030), where lactate (or ionic strength) in the fluid sample would be near or equal to the concentration of lactate (or other draw solution) in the concentrator pump 1097. Lactate is not the only possible example, since $Na^+$ and $Cl^-$ are also possible targets, especially if draw materials utilize materials such as $MgCl_2$ or $CeCl_3$ which will have greater difficulty leaking back into the fluid sample from the concentrator pump 1097 (divalent cations, etc.). Alternatively, uncharged solutes can be used, including sugars. Finally, polyelectrolytes, both positively and negatively charged, can be used as additional draw solutions including but not limited to polyacrylic acids, polysulfonic acids, polyimidazoles, polyethylenimines, etc. The disclosed invention may therefore provide a determined amount of sample concentration, where at least one first solute in the concentrator pump is also a solute in the fluid, and the concentration of the first solute in the concentrator pump is greater than that in the fluid by at least 2× to enable sample concentration by osmosis. The invention may also include at least one sensor to measure the first solute's concentration in an unconcentrated fluid sample.

Figure 11A:
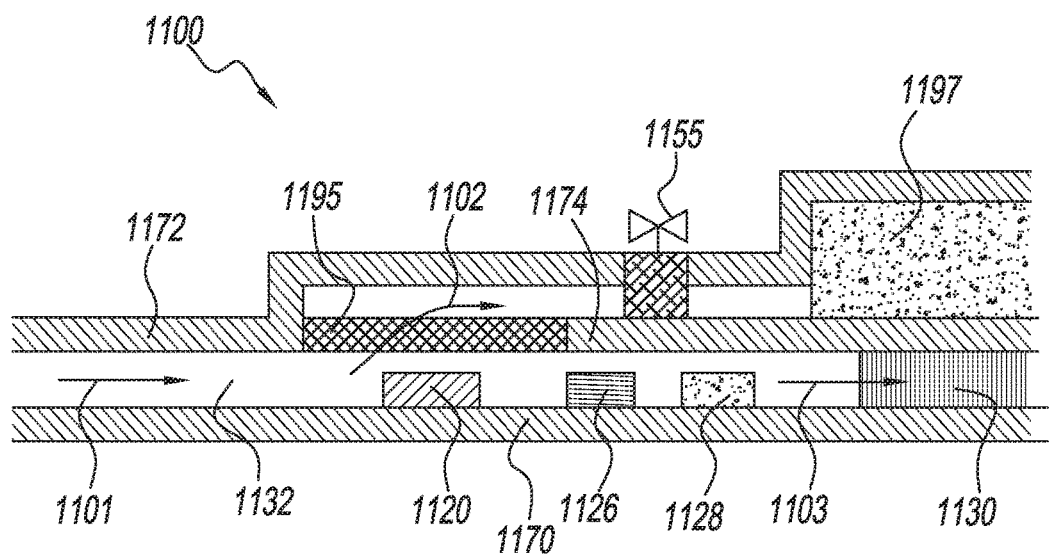
FIGS. 11A and 11B depict an example embodiment of at least a portion of a device capable of fluid sample concentration.

With reference to FIG. 11, where like numerals refer to like features of previous figures, a device 1100 includes an incoming flow path 1101 and two exit flow paths 1102, and 1103. A microfluidic or other type of controllable valve 1155, such as a PDMS pneumatic control valve, is provided to control fluid flow to concentrator pump 1197. In one example embodiment, the draw rate of concentrator pump 1197 would be sufficient to reduce fluid flow through path 1103 to zero if valve 1155 were fully opened. The device therefore works as follows: sensors 1126 and 1128 detect the presence of fluid, and are used to provide feedback control for valve 1155. Valve 1155 would be configured to control fluid flow so that sensor 1126 is wetted by fluid, but sensor 1128 remains unwetted. As a result, the device would ensure that at least one analyte-specific sensor 1120 is wetted by the fluid sample being concentrated. Using one or more techniques described herein, once the target analyte is sufficiently concentrated to allow the sensor 1120 to take an accurate reading, the valve 1155 may be partially or completely closed, restricting flow path 1102. Restricting flow path 1102 activates flow path 1103, and the (old) fluid sample moves away from sensor 1120 and onto fluid sample pump 1130. In this configuration, the device could repeatedly concentrate a fluid sample, sense the analyte, and then eliminate the fluid sample in preparation for another sensing event. Therefore, embodiments of the invention may include at least one tunable valve that controls the amount of sample concentration that occurs.

Figure 11B:
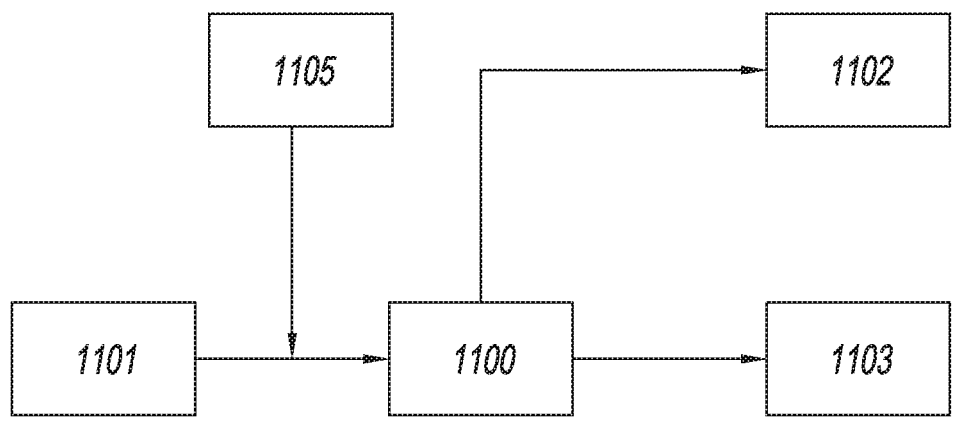

With reference to alternate embodiments, components taught for FIG. 11 may be extended to more general embodiments such as that illustrated in FIG. 11B. Component 1101 introduces the fluid to be measured, component 1105 introduces an unconcentrated fluid such as water, saline, buffer, or other fluid, component 1100 is where sample concentration may occur and where the amount of water loss due to concentration is regulated by component 1102, and component 1103 is a pump like that taught for previous figures. Therefore, the invention may include a plurality of valves, or an inlet valve for at least one unconcentrated fluid. In some embodiments, the sample concentration component could become clogged as a high concentration of solutes in the tested fluid build up. Therefore, component 1105 could introduce an unconcentrated fluid such as water, which could be used to flush the device and clear the highly concentrated solutes. FIG. 11B also generally teaches that valves and inlets could be placed at multiple locations. For example, component 1101 could have a valve that regulates the introduction of fluid sample into the device. Therefore, the disclosed invention may include at least one valve that controls the flow rate of a fluid that is unconcentrated.

Figure 12A:
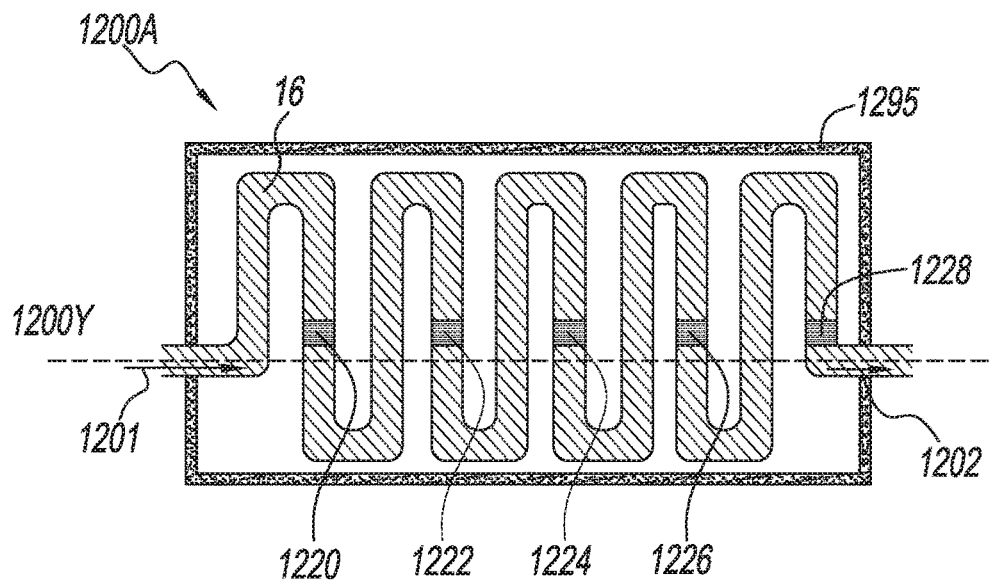
FIGS. 12A to 12C depict an example embodiment of at least a portion of a device capable of fluid sample concentration.
Figure 12B:
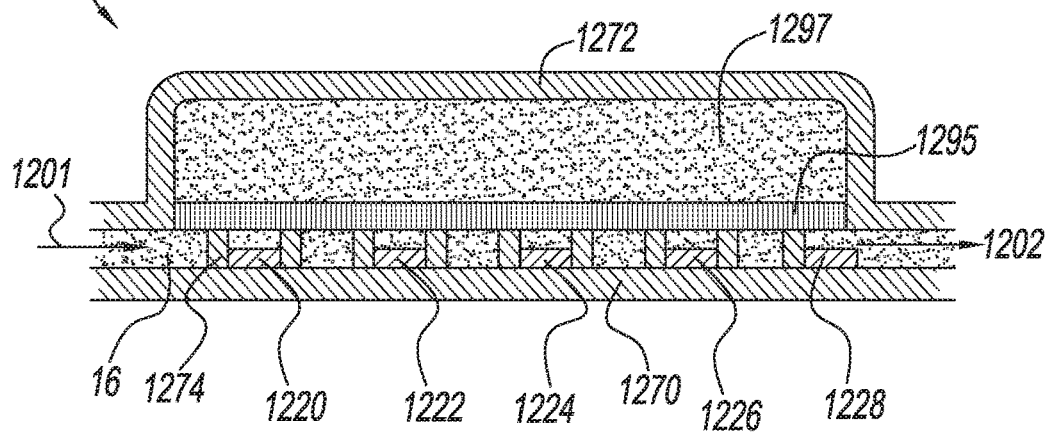

An example embodiment of the device described in FIG. 11 requires several controls and sensors that may be unnecessarily complex or sophisticated for some applications. With reference to FIGS. 12A and 12B, where like numerals refer to like features of previous figures, a simpler device 1200 includes a top view diagram 1200A and a side view diagram 1200B, which depicts a cross section of 1200A along axis 1200Y. A fluid sample 16 enters the device at opening 1201 and flows inside a channel that is constrained on its upper surface by a concentrator membrane 1295 or fluid impermeable material 1272, and ends in opening 1202. A plurality of sensors 1220, 1222, 1224, 1226, 1228 are provided within the channel. As the fluid sample 16 moves along the channel, a concentrator pump 1297 causes water (and in some embodiments certain small fluid-abundant solutes) to pass through the concentrator 1295. If the fluid flow rates are very low, then only sensors nearer to opening 1201, such as sensors 1220 and 1222, may experience analyte concentrations sufficient to allow accurate measurements. Sensors farther along the channel, such as 1226 and 1228, will remain unused if the fluid 16 does not reach them, or their data discarded if the analyte concentration remains inadequate. Conversely, at very high fluid flow rates, sensor 1228 may be the only sensor to receive sufficiently concentrated analytes. In some embodiments, opening 1202 could be configured adjacent to a fluid sample pump (not shown). Or concentrator membrane 1295 and concentrator pump 1297 could both concentrate the fluid sample and supply wicking pressure to move fluid 16 through the channel. A specific example may be taught through FIGS. 12A and 12B. Assume 2 nL/min/gland sweat generation rate, 10 eccrine sweat glands under the device, and sweat collected from 0.1 cm$^2$ area. This would provide a sweat flow rate of 20 nL/min, or 100 nL every 5 minutes. Assume 10,000× concentration of the fluid sample by the end of the channel (0.01 nL) and by the end of 5 minutes. Assume the draw rate of the forward osmosis concentrator membrane is 200 nL/min/mm$^2$ or 1000 nL/mm$^2$ every 5 minutes. Assume a channel that is 500 μm wide by 50 μm high, with additional spacers added to the middle of the channel if needed for support of the channel height. If the channel is 2 cm long, then it has a volume of 2·(500E-4)(50E-4)=5E-4 mL or 500 nL. This channel would tolerate a fluid flow rate up to a maximum of 10 nL/min/gland, which is unlikely to be encountered, meaning the channel as disclosed would be able to accommodate all typical sweat generation rates.

With further reference to FIG. 12, consider a case where the sensors are electrochemical aptamer-based sensors with an attached redox couple. Such sensors typically have a linear range of 80× the $K_D$ value for the target analyte. If 100× sample concentration were needed, as little as 2 to 3 sensors could achieve a proper reading within range. The distance between the sensors is known, and therefore the amount of concentration measured from sensor to sensor could be used to determine the flow rate through the channel (the concentrator membrane flow rate out of the channel would also be known). This could then be used to back-calculate the original analyte concentration in the fluid sample. Furthermore, flow rate could be determined by simply knowing which sensors are wet with a sample of fluid, which would then allow calculation of the flow rate of fluid coming into the concentration portion of the device. Therefore, the disclosed invention may include a plurality of sensors that determine a fluid flow rate into the device by measuring an unconcentrated analyte concentration and comparing it to a concentrated analyte concentration. Furthermore, if the length of the channel is known, and the concentration difference between successive sensors measured (e.g., between 1222 and 1224), then the device may determine the concentration increase per unit length of channel, and thereby determine the total amount of concentration increase at each sensor.

Figure 12C:
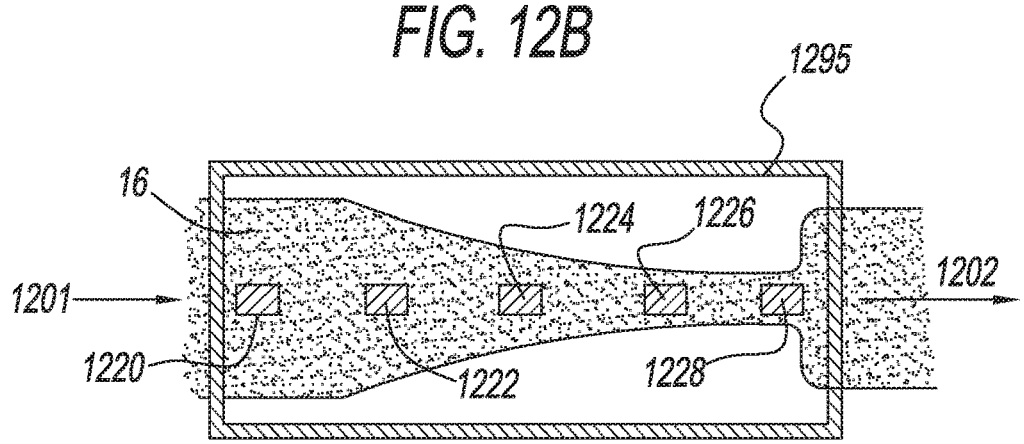

With reference to FIG. 12C, in an alternate embodiment, the channel containing fluid 16 can be tapered or geometrically reduced in any manner that minimizes the reduction in fluid flow velocity caused by volume loss as the fluid moves through the sample concentration component of the device and water is extracted by the concentrator membrane 1295. If a device achieved a high degree of fluid sample concentration, there could be very little fluid sample volume (and hence little fluid flow) left by the time fluid exits the concentration component. Therefore, to ensure an adequate flow of fluid through the device, the channel dimensions reduce along the channel in the direction of fluid flow.

Figure 13A:
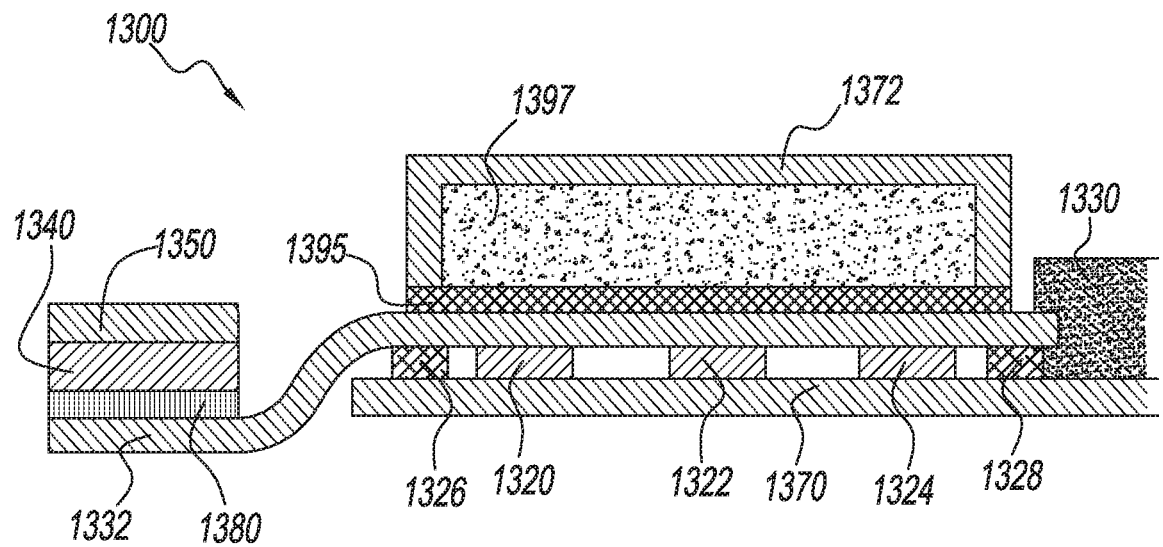
FIGS. 13A to 13D depict an example embodiment of at least a portion of a device capable of sweat sample concentration and which is additionally capable of sweat stimulation and/or reverse iontophoresis.

With reference to FIG. 13A, which is a variant of the previously taught FIG. 10, a device 1300 may include sweat stimulation and/or reverse iontophoresis or iontophoresis capabilities. For example, component 1350 could be an electrode, and component 1340 is an agar gel with pilocarpine or carbachol, and component 1380 is a track-etch membrane or other suitable membrane to reduce passive diffusion between the wicking component 1332 and the gel 1340. As a result, the device 1300 is capable of integrated sweat stimulation. Alternately, component 1340 could be a gel containing a buffer against pH changes, and electrode 1380 used to extract analytes in part from the body by reverse iontophoresis in order to increase their concentrations in sweat.

Figure 13B:
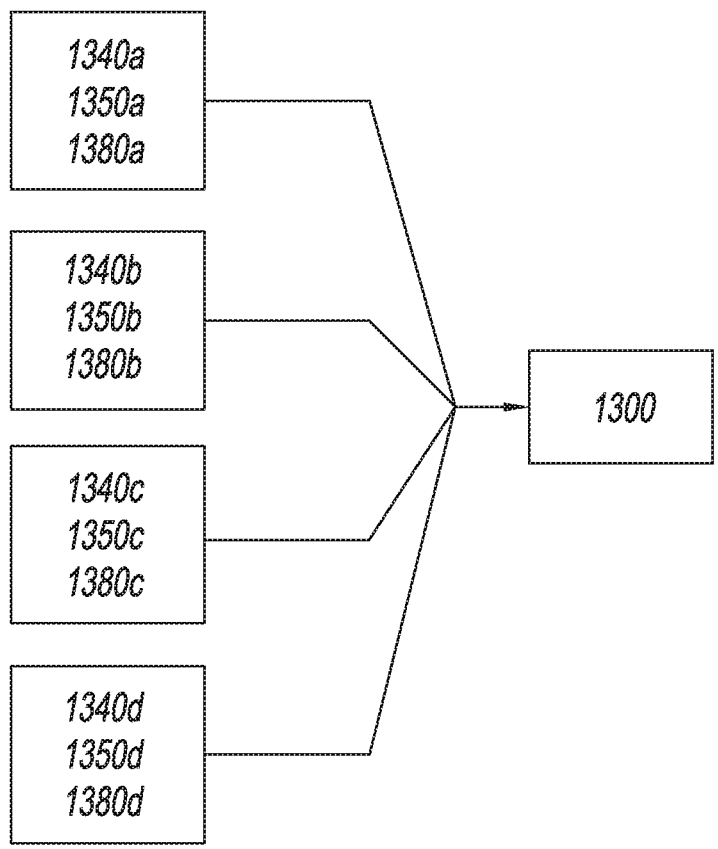

With reference to FIG. 13B, the components taught for FIG. 13A could be arranged such that plurality components for sweat stimulation or reverse iontophoresis (such as 1340a, 1350a, 1380a being one of such components) may feed into a common device 1300 that is capable of sample concentration. Such a design could prove useful, for example, where only a certain sweat flow rate into a device 1300 is needed and the number of sweat stimulation components utilized could be chosen to provide the most suitable total flow rate of sweat into the device 1300.

With further reference to FIG. 13B, multiple such components could also be used individually where sweat stimulation or reverse iontophoresis components could feed into sub-devices with their own sensors (e.g., a 1300a). Such an embodiment would be particularly useful where sub-devices such as 1300a, 1300b, 1300c, etc., are lateral flow assays or other sensor modalities that can be utilized only once.

Figure 13C:
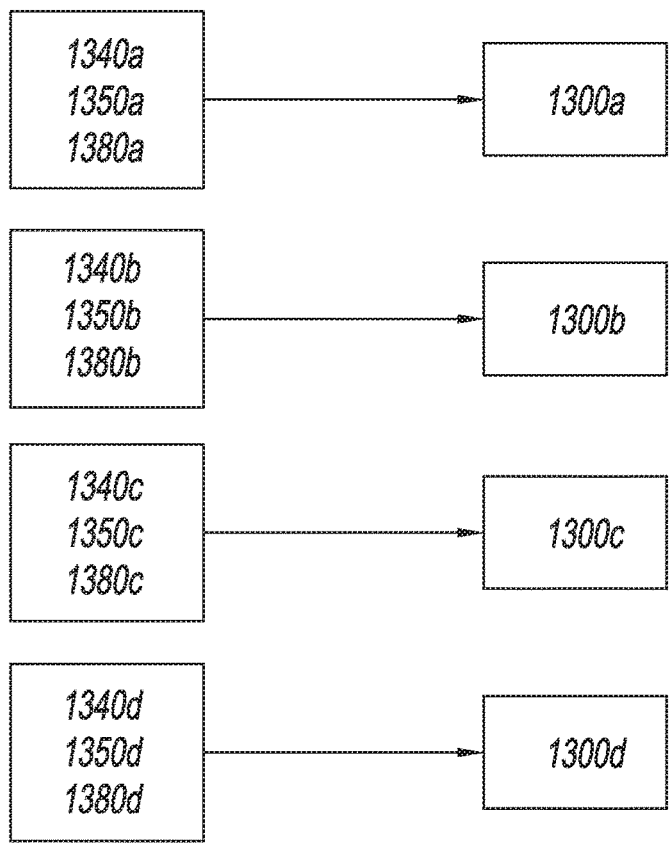
Figure 13D:
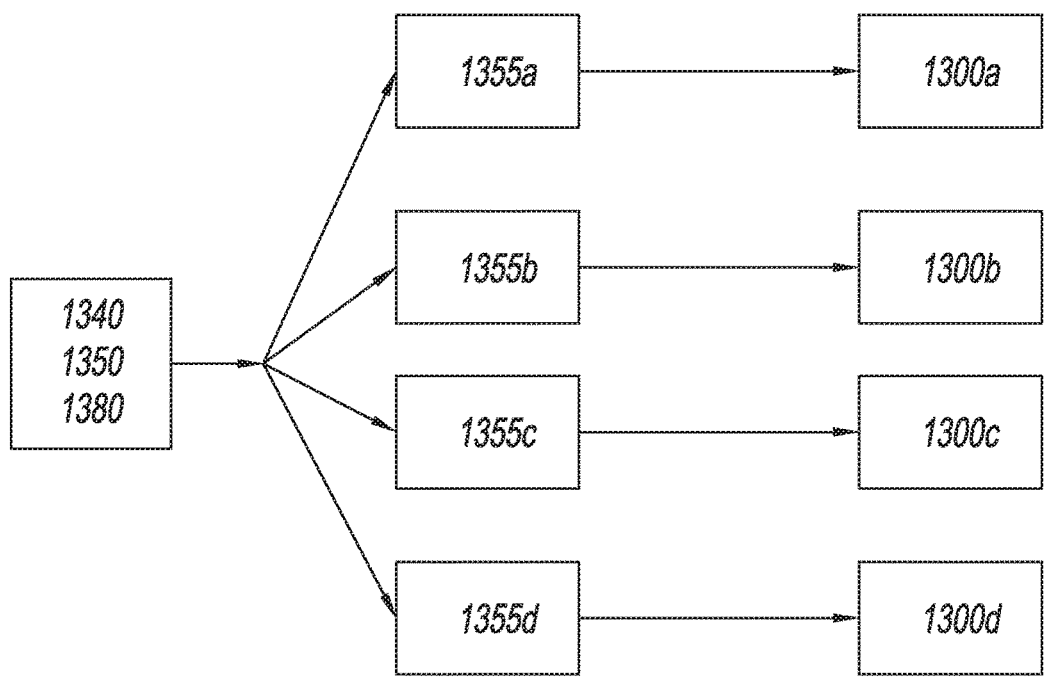

With reference to FIG. 13C, in yet another alternate embodiment, multiple valve components (1355a, 1355b, 1355c etc.) could be used to control, initiate, or stop flow of sweat to one or more sub-devices 1300a, 1300b, 1300c, etc. In this example, sweat comes from a single common component 1340, 1350, 1380, but could also use multiple sources as taught for FIGS. 13B and 13C.

In one embodiment, a functionalized silica gel, silicon dioxide nanoparticles, or other suitable substrate, can be added to a concentrator channel surface so that the surface has a high affinity for a target analyte through physi-sorption or chemi-sorption. Such a functionalized surface becomes the stationary phase of the concentrator channel. When fluid, as the mobile phase, is introduced into the device and flows past the surface, the target analyte is retained on the surface while the fluid continues to flow. The surface may be forced to release the target analyte by changing the fluid composition, e.g., by adding a solvent, changing the pH, changing solute concentrations, changing temperature, introducing electromagnetic radiation, or other system parameter. If the substrate is in the proper form, such as a bead or nanoparticle, multiple configurations may be present within the same concentrator/retarder system. This will allow the system to simultaneously concentrate multiple analytes using a single channel or using at least fewer channels than target analytes. The device as disclosed can be used to increase the concentration of analytes of interest, functioning similarly to the way a chromatography column is used for purification.

Figure 14A:
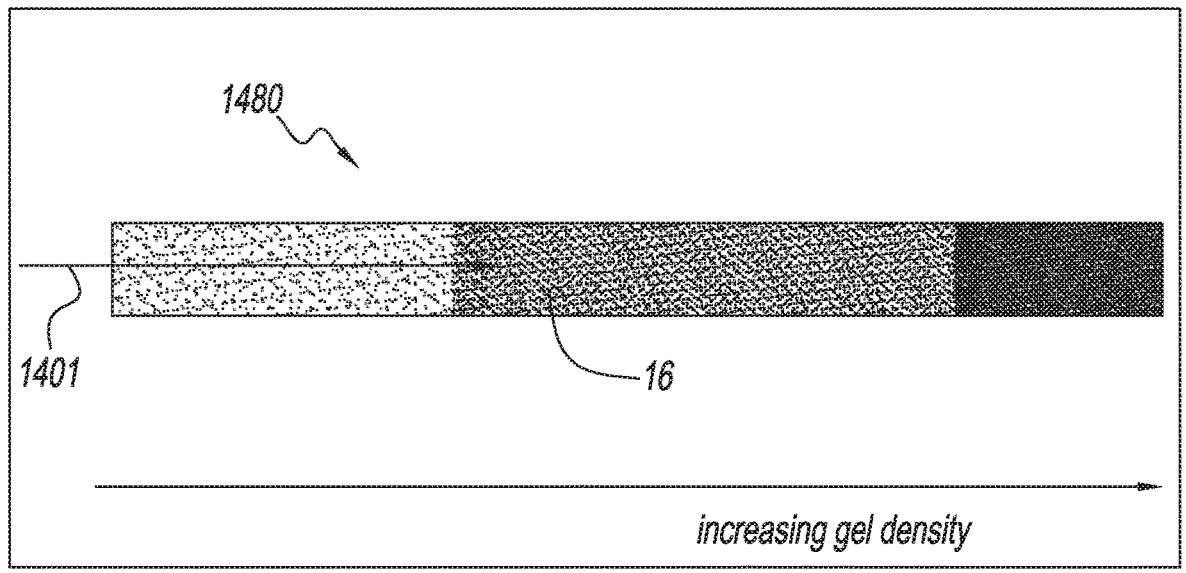
FIGS. 14A and 14B depict an example embodiment of at least a portion of a device capable of fluid sample concentration.
Figure 14B:
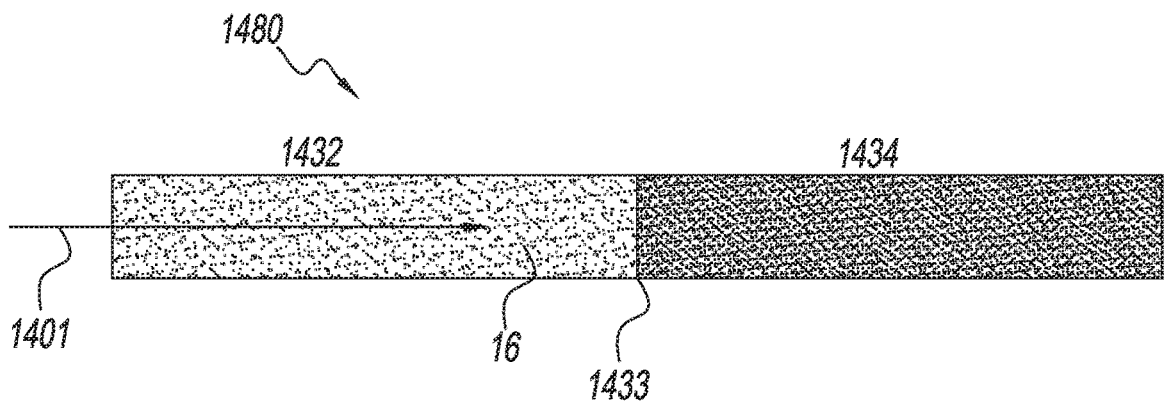

With reference to FIG. 14A, another embodiment of the disclosed invention would use a microfluidic channel 1480 that includes a gel (or other medium) that possesses a gradient in density or pore size in the direction of the fluid flow 1401. The pore size may be tuned to correlate with the size of one or more target analyte(s). As the fluid flows through the gel, the analytes that are larger than the pores will move slower than the flow rate. As the pore size decreases, the analyte flow rate will therefore decrease proportionally. As the analyte flow rate slows relative to the fluid flow rate, the analyte will gradually become concentrated in the direction of flow 1401. A similar embodiment depicted in FIG. 14B would configure two or more gels (or other media) with different densities in the microchannel 1480. As depicted, a first section 1432 has a first density, and a second section 1434 has a second, greater density. Step edges of increasing densities are thereby created at the boundary 1433 between the sections. These step edges will cause the analyte to concentrate at the boundaries and move at a slower rate in the next section. The result is a "wave front" in the microchannel in which the target analyte exists at a higher concentration than it occurs in unconcentrated fluid. Sensors could be placed within these sections to characterize the analyte concentration factor to facilitate converting the concentrated value back to the unconcentrated value.

Figure 15A:
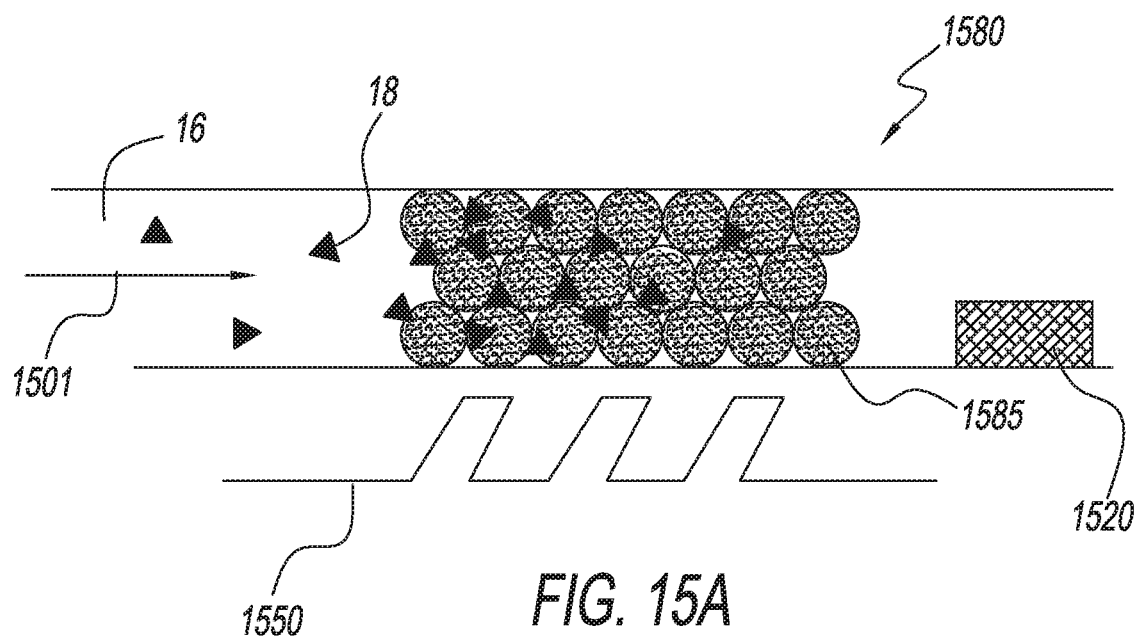
FIGS. 15A and 15B depict an example embodiment of at least a portion of a device capable of fluid sample concentration.
Figure 15B:
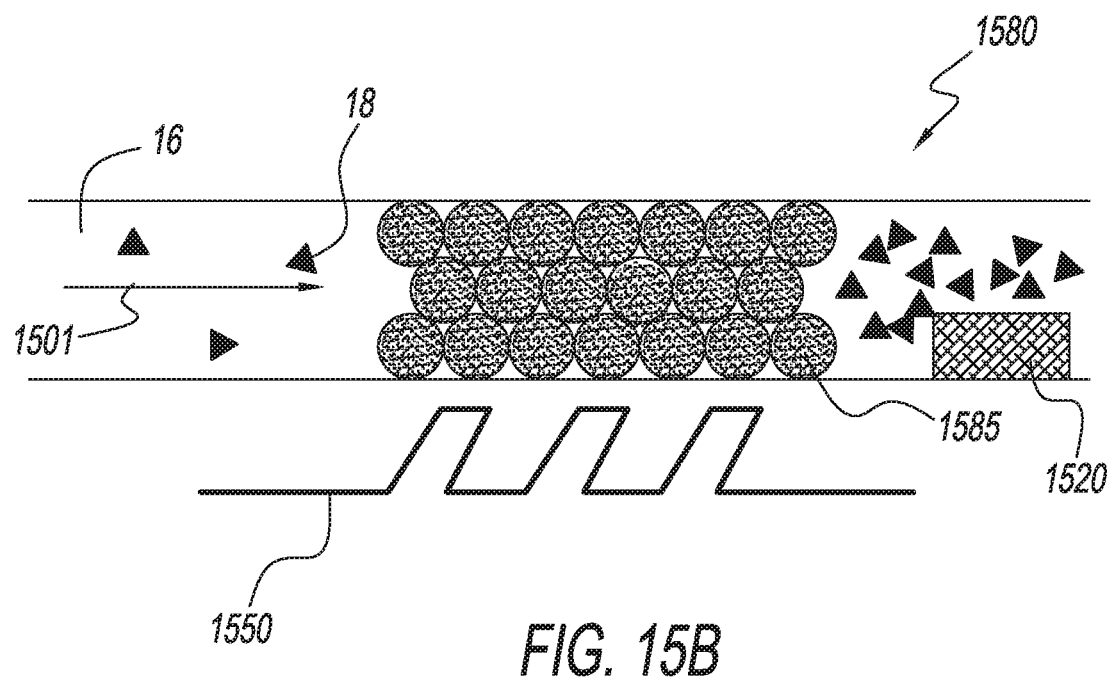

With reference to FIG. 15A, another embodiment illustrating fluid sample concentration includes a microfluidic channel 1580 with a plurality of microfluidic capture beads 1585. As a fluid sample 16 flows through the channel 1580, molecules of the target analyte 18 are trapped by the capture beads 1585. The embodiment further includes an analyte-specific sensor 1520 for measuring the target analyte, well as a heating element 1550. With reference to FIG. 15B, the fluid sensing device activates the heating element 1550, causing the target analyte molecules 18 to dislodge from the beads 1585 and flow with the fluid sample across the sensor 1520.

There are many applications where samples must be concentrated before analysis, including, without limitation, biofluids, waste water, municipal water, environmental sources, as well as food safety and/or quality applications. The embodiments of the disclosed invention apply broadly to these other fluid and analyte systems, and other point-of-use scenarios, so long as they rely on similar mechanisms for integrated sample concentration and analyte sensing. Not all embodiments will be taught in this way, rather it will be obvious from the additional specification below how all embodiments may cover more broadly other fluids, analytes, and point-of-use scenarios with minimal modification.

With further reference to FIG. 3B, for example, the fluid sample 16 may be a liquid food sample of a variety of viscosities, including without limitation, condiments, juices, and sodas. Sensors 320, 322, 324, 326 may be configured to measure one or more analytes relevant to food safety and/or quality.

With further reference to FIG. 7, an embodiment of the disclosed invention is configured to collect and measure analytes in non-sweat biofluids, such as saliva or interstitial fluid. At low concentrations of an analyte, there may be no signal change (the concentration is below the limits of detection) and at high concentrations, sensor signals can become saturated. The fluid sensing device may measure continuously or repeatedly to determine whether relatively linear windows (Windows 1 and 2) are achieved as shown in FIG. 7. As for the example of $K^+$ in sweat, a similar strategy of evaluating the degree of biofluid concentration by examining the concentration of a reference analyte that remains stable under most physiological conditions may be employed. For example, albumin concentration in blood remains relatively constant under most physiological conditions, and consequently, albumin concentration in most biofluids remains stable. Therefore, the increase in albumin concentration may be used as a measure of the extent of concentration for most biofluids. Similar reference analytes exist for other fluids that will allow quantitative assessments of the degree of fluid concentration relevant to target analytes.

Figure 16:
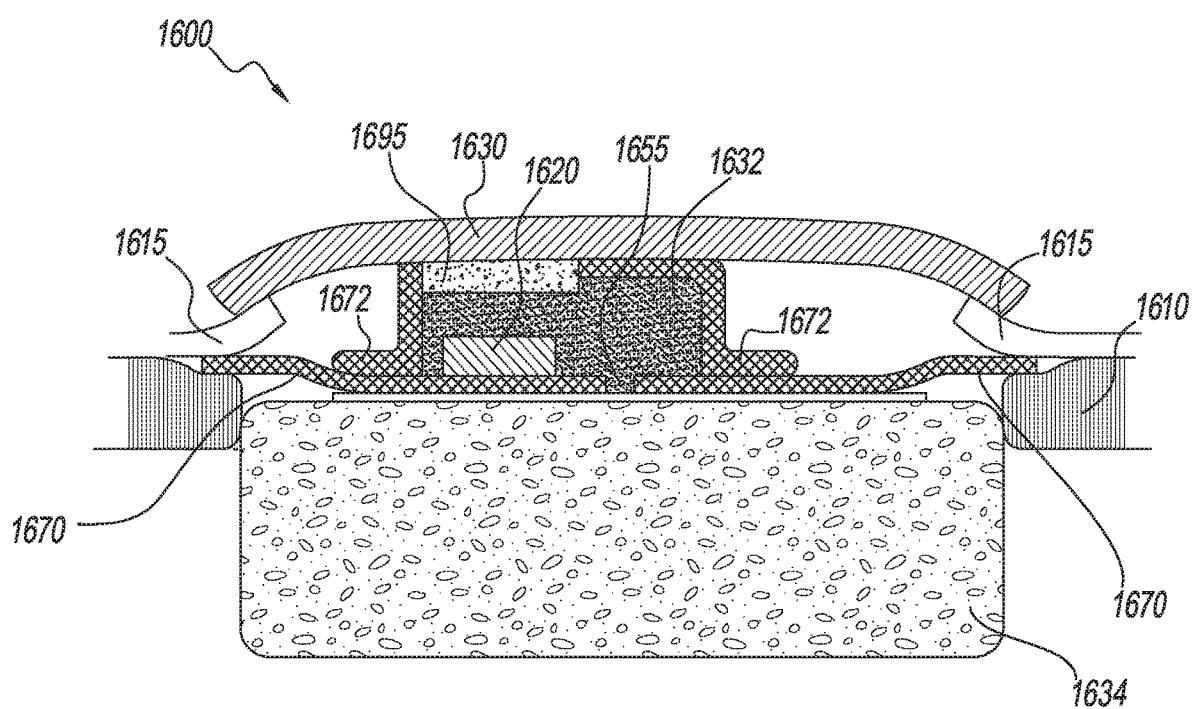
FIG. 16 depicts an example embodiment of at least a portion of a device capable of fluid sample concentration.

With reference to FIG. 16, where like numerals refer to like features and functions for FIG. 2, a device 1600 provides a wicking material such as a sponge 1634 configured to collect a sample fluid, such as river water, by placing the sponge into the river water (not shown). The river water would flow into the fluid sample coupler 1632 and across the sensor 1620. Water in the sample is drawn into pump 1630 through sample concentrator 1695 and is concentrated with respect to one or more target analytes, such as *Cryptosporidium* or one of that organism's products or toxins, and sensor 1620 then measures the analyte's concentration, or detects the analyte's presence, as the river water sample concentrates.

With further reference to FIG. 6, the device 600 is configured to detect microbes in a fuel sample. For example, modern biodiesel is especially hygroscopic. The presence of water encourages microbial growth, which either occurs at the interface between the oil and water or on the tank walls, depending on whether the microbes need oxygen. In this case, the device 600 is placed in contact with the fuel within the tank, or a stream of fuel (e.g., a hose transporting the fuel). Microfluidic channel 680 would contain the fuel brought into the device, and the immiscible material 655 would be non-dissolvable in the fuel. In contrast to the disclosed device's use in sweat, the immiscible material 655 may be hydrophilic (e.g., a hydrogel with water), which would passively concentrate the target analyte by distribution coefficient compared to the fuel. The sensor 620 could then detect the target analyte. The analyte could be bacteria, fungi, their toxins, or their other products.

With further reference to FIG. 10, the device 1000 is configured to detect a target analyte associated with a sexually transmitted disease, such as chlamydia or gonorrhea. The user would urinate onto wicking material 1032, and the device would concentrate and sense antigens or other target analytes. Sensors 1026 and 1028 could be chloride sensors (bare Ag/AgCl electrodes) whose ratios of potential determine the degree of concentration occurring. Sensors 1020, 1222, 1024 are configured to detect the disease analyte, and further, each sensor 1020, 1022, 1024 may be configured to detect the disease analyte at different concentrations. Such an arrangement would be useful for the described example, because the user would be able to have dilute urine or concentrated urine, and the device can accommodate this by operating over a wider range of these conditions for analyte concentration.

The following examples are provided to help illustrate the disclosed invention, and are not comprehensive or limiting in any manner. These examples serve to illustrate that although the specification herein does not list all possible device features or arrangements or methods for all possible applications, the invention is broad and may incorporate other useful methods or aspects of materials, devices, or other embodiments that are readily understood and obvious for the broad applications of the disclosed invention.

Example 1

This example provides additional examples of membranes suitable for the disclosed invention, including calculations of criteria related to membrane operation in the invention. Membranes of this and previous embodiments may utilize any material or filtration technique known by those skilled in the art of sample concentration or microfiltration. Solutes or analytes may be small ions, ions, small molecules, proteins, DNA, RNA, micro RNA or DNA, peptides, lipids, or any other solute or analyte of interest in sweat. Commercially available ultrafiltration and filtration membranes are most effective for larger solutes found in sweat, like proteins or peptides. Smaller molecules, including hormones and nucleotides, however, present a challenge, as they will typically pass through such membranes. Furthermore, if a membrane is used to block small molecules, but pass only water, then the concentration of salts, lactic acid, and other sweat-abundant analytes could fall out of solution or hinder proper device or sensor performance. Other options, such as aquaporin and other lipid membranes, perform no better with small molecules that are lipophilic, and further tend to have limited shelf-lives caused by a tendency to dry out unless stored wet, among other things. Embodiments capable of sampling smaller sweat analytes may therefore employ a membrane capable of forward osmosis (FO). Examples include a cellulose triacetate filter, like those produced by Hydration Technology Innovations; or the Dow Filmtec™ NF90-4040, a composite membrane made up of a polyamide active layer and a polysulfonic supporting layer, which works at low operating pressures. See A. Alturki, et al., "Removal of trace organic contaminants by the forward osmosis process" Separation and Purification Technology, 103 (2013) 258-266.

Such membranes can pass lactic acid (lactate), which is electrically charged and only 90 g/mole, or urea at 60 g/mole, as well as numerous salts in sweat. These solutes are found at higher sweat concentrations, so that if a sweat sample were concentrated 100×, their concentrations would correspondingly increase to the 1 M range, which could hinder device performance in one or more ways. Therefore, having a membrane that can concentrate the sweat sample while allowing these solutes to pass through is advantageous. Further, the membrane must have high rejection rates for solutes of interest. For example, a small molecule like cortisol is uncharged, hydrophobic, and ~362 g/mole, and therefore would be substantially rejected by the membrane and concentrated in the sweat sample to be analyzed. In addition, this would allow for a second reference sensor next to each analyte sensor (as taught in previous figures). An example would be sensing changes in cortisol, and using cholesterol as a reference, because cholesterol is lipophilic and nearly identical to cortisol in molecular weight, and suitable sensors exist for cholesterol.

When operated in FO mode, i.e., with the membrane's dense side facing the sweat sample to be concentrated, or feeder solution, and the membrane's porous side facing the concentrated draw solution, these materials are capable of processing a ~1 M NaCl solution with a flux near 200 nL/min/mm$^2$. If the sweat sensor device's microfluidic channel were 20 μm wide, each 1 mm$^2$ of that channel would have a sweat volume of 20E−4 cm·0.1 cm·0.1 cm=2E−5 mL or 20 nL. Therefore, to achieve a sample concentration of 10×, the device would require, at most, a sweat generation rate of approximately 20 nL/min/mm$^2$. If, through the use of lower sweat volumes, the device was capable of fast sweat sampling rates, e.g., every 5 minutes, then only 4 nL/min/mm$^2$ of sweat would be required. Sweat generation rates in this range would allow concentration to occur at very low osmotic draw pressures, eliminating or reducing the need to augment draw pressures through the addition of a sugar (sucrose or glucose), or a salt, such as MgSO$_4$, to the draw solution.

While having a low osmotic pressure is desirable from a sweat generation rate standpoint, osmotic pressure across the membrane still must be greater than the wicking pressure provided by sweat collecting components, otherwise, the water in sweat would not pass through the membrane. From A. Alturki, et al., osmotic pressure for a 0.5 M NaCl solution (with van't Hoff factor of 2) would be as follows: Π=iMRT=2·(0.5 mol/L)(0.0821 L atm/mol/K)(298 K)=24.5 atm. Similarly, osmotic pressure for 0.5 M sucrose solution (with van't Hoff factor of 1) would be: Π=MRT=1·(0.5 mol/L)(0.0821 L atm/mol/K)(298 K)=12.2 atm. To calculate the osmotic pressure achieved by adding saturated sucrose to drive sweat across the membrane, the sucrose solubility limit in water is 2000 g/L/(342.30 g/mol)=5.8 mol/L or 5.8 M. Therefore, adding sucrose would provide osmotic pressures of around 141 atm or 101,000 N/m². Typical wicking pressures would be an order of magnitude lower. For example, pressure for a 20 μm high wicking channel (r=10 μM) would be (73E-3 N/m)/(10E-6 m)=7300 N/m² (14× less). Likewise, if using a 10×10 μm sweat collector groove, the wicking pressures would be comparable to the 20 μm channel. Therefore, osmotic pressures for this embodiment of the invention would be sufficiently higher than wicking pressures to allow the FO membranes to function. Therefore, the invention may include a sample concentration component and at least one sweat wicking component, where said concentration component has an osmotic pressure that is at least 2× greater and preferably 10× greater than wicking pressure of said wicking component.

If needed, draw pressures may also be augmented by adding capillary wicking pressure to the draw side of the membrane through use of microfluidics. Some embodiments may use osmotic pressure, wicking pressure, or a combination, to drive sweat across the membrane, depending on the application. Therefore, the invention may also include a draw material that contains a wicking material that operates by capillary wicking pressure. Considerations determining the choice of method would include the need to drive sweat abundant solutes, i.e., $Na^+$, $Cl^-$ and $K^+$, across the membrane to avoid fouling the concentrated sweat sample. Also, sweat sensor devices with larger sweat volumes may require additional draw pressures to sense a given analyte. And certain sweat applications may require or otherwise be limited to lower sweat generation rates, which would also require higher draw pressures.

The above example can provide sample concentration for even challenging analytes such as cortisol (362 Da), especially if a similar analyte, i.e., cholesterol (387 Da) is also measured as a reference analyte, because it has a very low diurnal change (e.g., compare ratios of the two analytes). For example, if the membrane is cellulose acetate (which is very hydrophilic) lipophilic analytes such as cortisol could achieve 70 to 95% rejection or even greater. The above example will remove water, and the above example can also remove $Na^+$, $Cl^-$, $K^+$, lactate (90 Da), urea (60 Da), and other high-concentration analytes that might be undesirable if they were also concentrated in the sweat sample. The above examples could work well with draw solutions that are monosaccharides or disaccharides (100's of Da). Amino acids are also found in sweat up mM levels. Many amino acids are small, and will readily pass through a membrane. Assume average of 0.1 g/mL solubility limit, and average 100 g/mol. The molar concentration is 0.1×1000 g/L/(100 g/mol)=1 mol/L or 1M. Therefore, sweat could be concentrated by nearly 1000× before amino acids would fall out of sweat due to their solubility limits.

Example 2

This example provides additional examples of membranes suitable for the disclosed invention, including in some cases calculations of criteria related to their operation in the invention. More specifically, this example teaches an exemplary case for a determined amount of concentration as taught for FIG. 10. Assume a hydrophilic channel that is 7 μm tall, and 500 μm wide and which has a wicking pressure of ~20,000 N/m². Assume a membrane that as biologically inert and ultra-pure, such as Biotech Cellulose Ester (CE) membranes, which offer a large range of concise molecular weight cut-offs (100 to 1,000,000 Da) and that tolerates weak or dilute acids & bases, as well as mild alcohols. For example, choose a molecular weight cut-off of ~500 Da. Assume a concentrator pump with a draw material that is 7 mM of polyethylenimine in water and/or other suitable solvent with a molecular weight of ~10,000 Da, and the draw solution may also contain other solutes found in natural sweat (pH, salts, etc.) that may be desirable for proper sensor function or for other purposes. If each monomer of polyethylenimine, which is a polyelectrolyte at pH<10, has a molecular weight of ~50 Da, then there are ~200 positive charges, and thus 200 counter-ions, likely chloride at pH values relevant to sweat (assume pH 6.5). Assuming full disassociation at the pH's observed in sweat, this draw solution would yield an osmotic pressure against natural sweat equivalent to about 10× greater the osmotic pressure that sweat can generate. Therefore, the sweat will be concentrated about 10× for solutes that are >500 Da in size, and for the numerous solutes <500 Da they will largely be absorbed into the draw material through the membrane. However, this would generally require, that for continuous operation, the volume of the draw material should be very large compared to the total sweat sample collected (else the osmotic pressure difference will degrade over time). For example, the volume of the draw material could be 2× or 10× greater than the total sweat sample volume collected, and more preferably >100× or even >1000×. Polyethylenimine is not a natural solute in sweat. The disclosed invention may also therefore provide a determined amount of sample concentration, where the total osmolality of the concentrator pump is at least 2× greater than the total osmolality of sweat. Still, a question remains as to how the osmolality differences between polyethylenimine draw solution and natural sweat can be determined, because if the osmolality difference is not determined, then the amount of concentration occurring is more difficult to directly predict unless some other prediction method (including those taught herein) is utilized. One example method which would work with multiple figures and embodiments of the invention, would be to have at least one sensor which measures the total osmolality of the natural sweat coming into the device, using methods such as measuring total electrical conductance of sweat, or by having a common pressure sensor which is surrounded (covered) by a membrane which passes mainly water and with an internal draw solution or material which therefore causes pressure sensor to directly measure osmotic pressure and therefore osmolality of sweat. For even greater precision, especially if the osmolality of the draw material/solution changes over time, such types of osmolality sensors may also be placed in the concentrator pump.

This has been a description of the disclosed invention along with a preferred method of practicing the disclosure, however the invention itself should only be defined by the appended claims.

What is claimed is:
1. A sensing device configured to receive a fluid sample, the sensing device comprising:
   one or more first analyte sensors for measuring a characteristic of a first analyte in the fluid sample;

a sample concentrator configured to generate a concentrated form of the fluid sample to increase a first molarity of the first analyte within the fluid sample to a second molarity, wherein the second molarity is at least two times higher than the first molarity, the sample concentrator comprising a membrane that is permeable to liquid and impervious to the first analyte, the membrane having a first surface adjacent to the fluid sample and a second surface opposite the fluid sample;

a collector for collecting the fluid sample from a body of a sensing device wearer;

a channel for transporting the fluid sample from the collector to the sample concentrator, to the one or more sensors, and away from the one or more sensors.

2. The sensing device of claim 1, further comprising:
one or more second analyte sensors for measuring a second analyte in the fluid sample, and wherein the sample concentrator is further configured to concentrate the fluid sample to increase a third molarity of the second analyte within the fluid sample to a fourth molarity, wherein the fourth molarity is at least two times higher than the third molarity, and wherein the membrane is further configured to be impervious to the second analyte.

3. The sensing device of claim 2, wherein a ratio of the first molarity to the second molarity is substantially equal to a ratio of the third molarity to the fourth molarity.

4. The sensing device of claim 1, wherein the sample concentrator further comprises:
a pump configured to draw water and/or fluid sample-abundant solutes through the membrane to concentrate the fluid sample relative to the first analyte.

5. The sensing device of claim 4, further comprising:
an osmolality sensor configured to measure a total osmolality of the pump.

6. The sensing device of claim 1, further comprising:
a flow-rate sensor for measuring a rate of movement of the fluid sample through the sensing device, wherein the rate of movement is measured at one of the following: prior to the sample concentrator, or after the sample concentrator.

7. The sensing device of claim 1, the one or more first analyte sensors further comprising:
a primary sensor and a secondary sensor, wherein the primary sensor has a dynamic range configured for use on a first concentration of the first analyte, and the secondary sensor has a dynamic range configured for use on a second concentration of the first analyte, wherein the second concentration is greater than the first concentration.

8. The sensing device of claim 1, further comprising:
an osmolality sensor configured to measure a total osmolality of the fluid sample.

9. The sensing device of claim 1, wherein the sample concentrator further comprises:
a concentrator channel including one of: an increasing density gradient within the concentrator channel that is oriented in a direction of fluid sample flow, a plurality of different densities within the concentrator channel that create a stepped increasing density gradient oriented in the direction of fluid sample flow, and a plurality of pores configured to interact with the first analyte as the fluid sample flows through the concentrator channel.

10. The sensing device of claim 1, further comprising:
one or more of: a sweat stimulation component comprising a chemical capable of sweat generation and an iontophoresis electrode, or a reverse iontophoresis component configured to move the fluid sample into the device.

* * * * *